(12) United States Patent
Vreugdenhil et al.

(10) Patent No.: US 7,754,871 B2
(45) Date of Patent: Jul. 13, 2010

(54) MRNA SPLICE VARIANT OF THE DOUBLECORTIN-LIKE KINASE GENE AND ITS USE IN CANCER DIAGNOSIS AND THERAPY

(75) Inventors: Erno Vreugdenhil, Leiden (NL); Petra Van Kuik-Romeijn, Utrecht (NL)

(73) Assignees: Prosensa B.V., Leiden (NL); Universiteit Leiden, Leiden (NL)

( * ) Notice: Subject to any disclaimer, the term of this patent is extended or adjusted under 35 U.S.C. 154(b) by 0 days.

(21) Appl. No.: 11/186,807

(22) Filed: Jul. 22, 2005

(65) Prior Publication Data
US 2006/0019924 A1 Jan. 26, 2006

(30) Foreign Application Priority Data
Jul. 22, 2004 (EP) .................................. 04077124

(51) Int. Cl.
*C07H 21/04* (2006.01)
*A61K 31/70* (2006.01)
(52) U.S. Cl. ......................... 536/24.5; 536/23.1; 514/44
(58) Field of Classification Search ........................ None
See application file for complete search history.

(56) References Cited

U.S. PATENT DOCUMENTS

| 7,250,496 B2 * | 7/2007 | Bentwich .................... 536/23.1 |
| 7,314,750 B2 * | 1/2008 | Zhou ........................ 435/287.2 |
| 2003/0119009 A1 * | 6/2003 | Stuart et al. ..................... 435/6 |
| 2004/0214325 A1 * | 10/2004 | Crooke et al. ............... 435/375 |

FOREIGN PATENT DOCUMENTS

| EP | 0 978 562 | 8/1998 |
| WO | WO 00/08151 | 2/2000 |
| WO | WO 03/018816 | 3/2003 |
| WO | WO 2004/045592 | 6/2004 |

OTHER PUBLICATIONS

Pagnan et al. Journal of the National Cancer Institute 2000, vol. 92, pp. 253-261.*
Burgess, H.A. et al., "KIAA0369, doublecortin-like kinase, is expressed during brain development" Journal of Neuroscience Research Nov. 15, 1999, vol. 58, No. 4, pp. 567-575.
Burgess, H.A. et al., "Doublecortin-like kinase is associated with microtubules in neuronal growth cones" Molecular and Cellular Neurosciences Nov. 2000, vol. 16, No. 5, pp. 529-541.
Engels, B.M. et al., "Functional differences between two DCLK splice variants" Molecular Brain Research Jan. 5, 2004, vol. 120, No. 2, pp. 103-114.
Héraud, C. et al., "Neuritogenesis Induced by Vasoactive Intestinal Peptide, Pituitary Adenylate Cyclase-Activating Polypeptide, and Peptide Histidine Methionine in SH-SY5Y Cells Is Associated with Regulated Expression of Cytoskeleton mRNAs and Proteins" Journal of Neuroscience Research Feb. 1, 2004 U.S., vol. 75, No. 3, pp. 320-329.
Matsumoto, N. et al., Genomic Structure, Chromosomal Mapping, and Expression Pattern of Human *DCAM KL1* (*KIAA0369*), a Homologue of *DCX* (*XLIS*) Genomics, Academic Press, San Diego, U.S., vol. 56, No. 2, Mar. 1, 1999, pp. 179-183.
Ohara, O. et al., "Homo sapiens mRNA for KIAA0369 gene, partial cds." Jul. 1, 1997 XP002300182.
Sossey-Alaoui, K. et al., "DCAM KL1, a Brain-Specific Transmembrane Protein on 13q 12.3 That Is Similar to Doublecortin (DCX)" Genomics, Academic Press, San Diego, U.S., vol. 56, No. 1, Feb. 15, 1999, pp. 121-126.
Strausberg, R.L. et al., "Mus musculus mRNA similar to double cortin and calcium/calmodulin-dependent protein kinase-like 1 (cDNA clonen MGC:63284 Image:6416546), complete cds." Database EMBL Apr. 12, 2003, XP002299956.
Vreugdenhil, E. et al., "Multiple transcripts generated by the DCAMKL gene are expressed in the rat hippocampus" Molecular Brain Research Oct. 19, 2001, vol. 94, No. 1-2, pp. 67-74.

* cited by examiner

*Primary Examiner*—Tracy Vivlemore
(74) *Attorney, Agent, or Firm*—Young & Thompson

(57) ABSTRACT

The present invention relates to novel nucleic acid and protein molecules and their use in neuroblastoma therapy and diagnosis.

16 Claims, 11 Drawing Sheets
(6 of 11 Drawing Sheet(s) Filed in Color)

Fig 1b

```
mouseDCL   1 MSFGRDMELE HFIEEDKAQKYS RGSKVRGLPSPTHSAHCSFYTRTLQIL  50
mouseDCX   1      MELDFCEETERKASRNM RGSRMAGLPSPTHSAHCSFYRTRTLQAL  46
               .. HFDERDKA R  RGSR.NGLPSPTHSAHCSFYRTRTLQ.L
                                              ←————— DCX domain I ————— mouseDCL  51 SIEKAKKVRFIRNGIRYFKGIVYAISP FEKAFEALLADEIFIEADNVN  100
mouseDCX  47 SNEKAKKVRFIYRNGDRYFKGIVYAVS DFEREFDALLADLTRSLSDNIN  96
             S  EKKAKKVRFYRNGDRYFKGIVYA.S  DRFRSF.ALLADLTR.LSDN.N
             ————————————————————→ mouseDCL 101 LPQGVRTITILDGLKKISELEQLVEGESYVCGSIEP FKKLEYTKNVNPNW  150
mouseDCX  97 LPQGVRYIYTIDGSREIGAMDELEEGESYVCSSDNF FKKVEYTKNVPNW   146
             LPQGVR YTIDG .KI S.D.L EGESYVC S  FKK.EYTKNVNPNW
                                                    ←————— mouseDCL 151 SVNVKTSASRAVSALATAKGGPSEV RENKDFIRPKLVTIIRSGVKPRKA  200
mouseDCX 147 SVNVKTSANMKAPQELASSNS--AQA RENKDFVRPKLVTIIRSGVKPRKA 194
             SVNVKT.. .A SLA..  ..  RENKDF RPKLVTIIRSGVKPRKA
                                ————————— DCX domain II ————— mouseDCL 201 VRILLNKKTAHSFEQVLTDITDAIKEDSGVVKREYTLDGKQVMCLQDFFG  250
mouseDCX 195 VRVLLNKKTAHSFEQVLTDITEAIKLETGVVKKLYTLDGKQVTCLHDFFG  244
             VR.LLNKKTAHSFEQVLTDIT.AIKL..GVVK.LYTLDGKQV CL.DFFG
             ——————————→ mouseDCL 251 DDDIFIACGPEKFRY.QDDFLDESECRVVES---TSYTKIASASRRGT   295
mouseDCX 245 DDDVFIACGPEKFRYAQDDFSLDENECRFMKGNPSAAAGPKASPTPQKTS 294
             DDD.FIACGPEKFRY QDDF LDE ECRV.K   . K
                                                ←————— SP-rich ————— mouseDCL 296 TKSPGPSRRSKSPASTSS---VNGTPGSQLSTPKGKSPSPSTSPGTERR  342
mouseDCX 295 AKSPGPMRRSKSPADSGNDQANTSSQLSTPKSKQSPISTETPGSLR    344
             .KSPGP RRSKSPA   NGT SQLSTP.S .SP .PTSPGSLR
             ————————————————→ mouseDCL 343 KQRIFYRPLSSDDLD.SGDAV 362
mouseDCX 345 RHKDLYLPLSLDDSDSL GDSM 365
             ...DLY PLS DD D GDS.
```

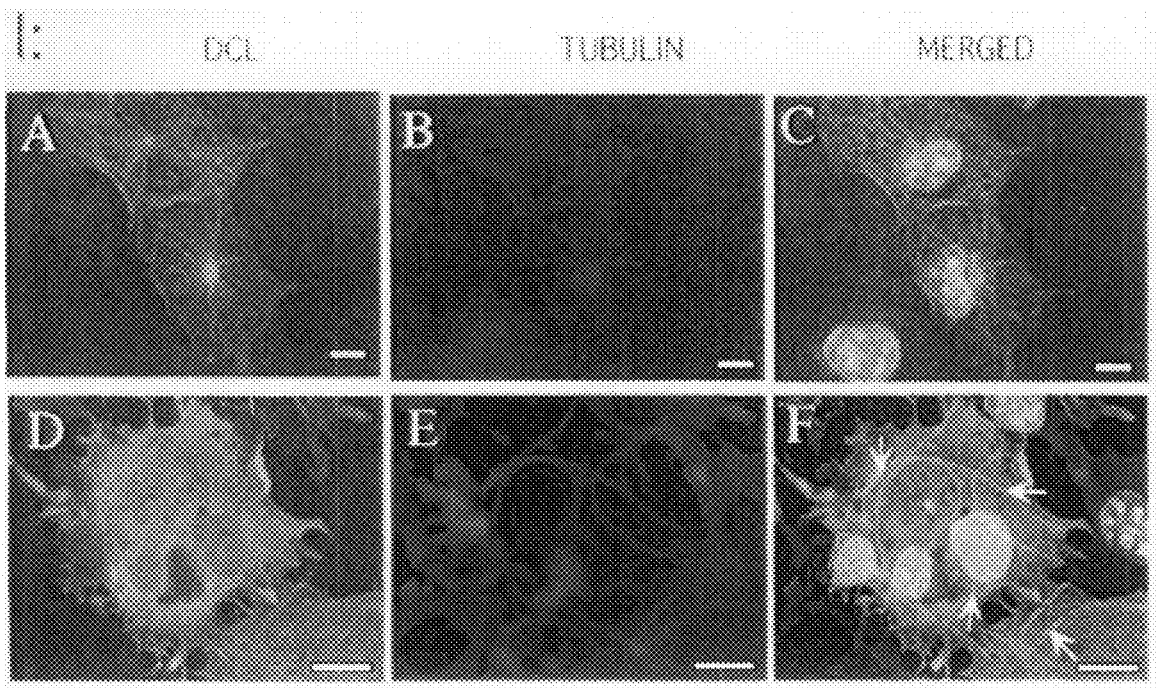
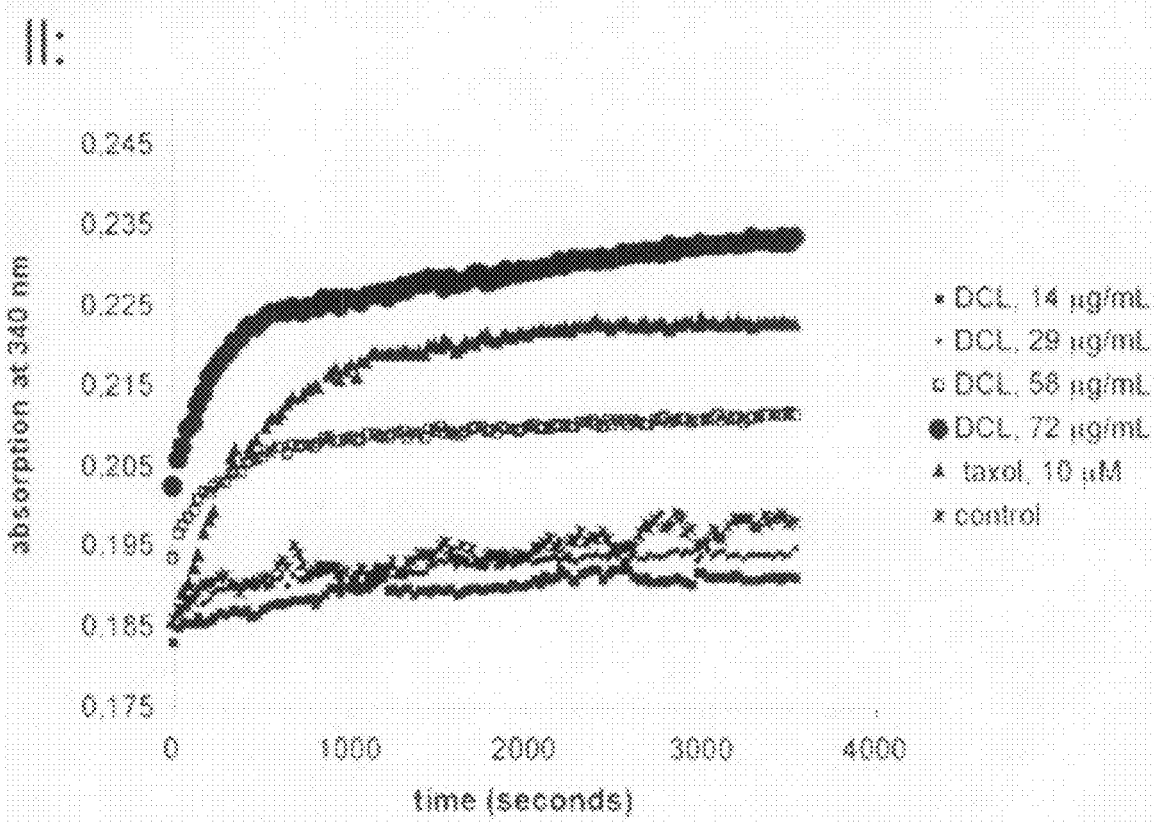
Figure 2

Fig 3
A
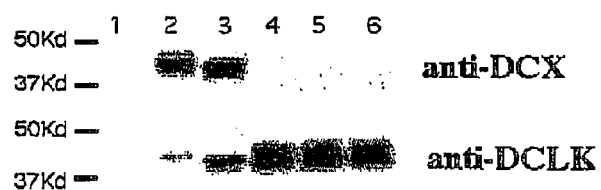
B
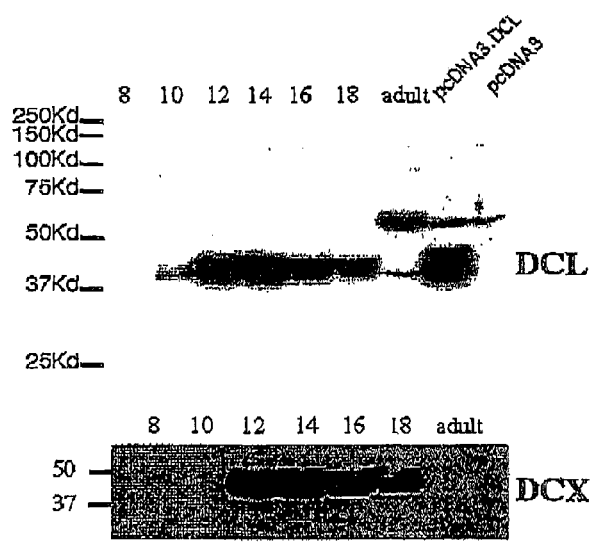
C

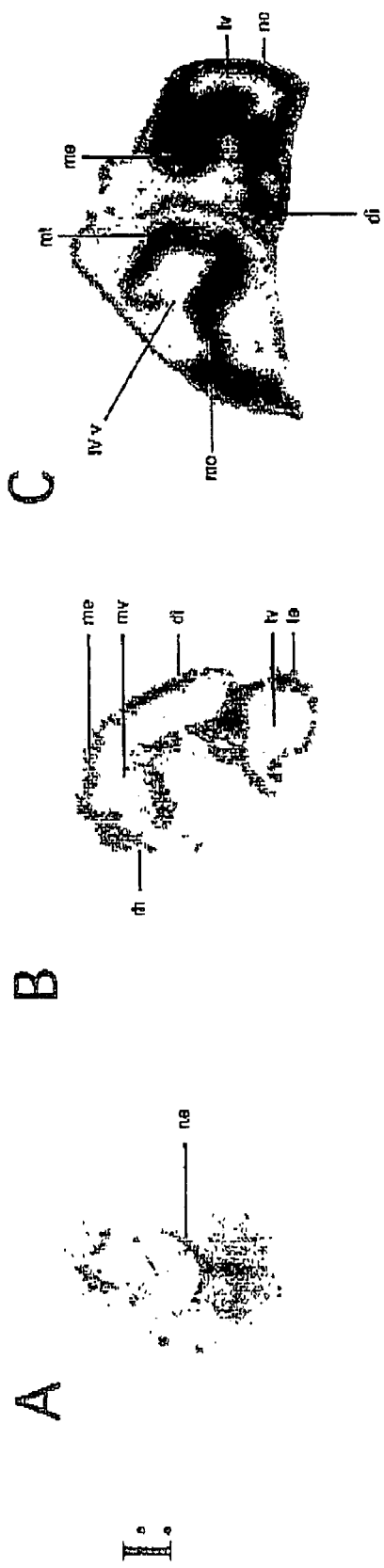

Figure 5:
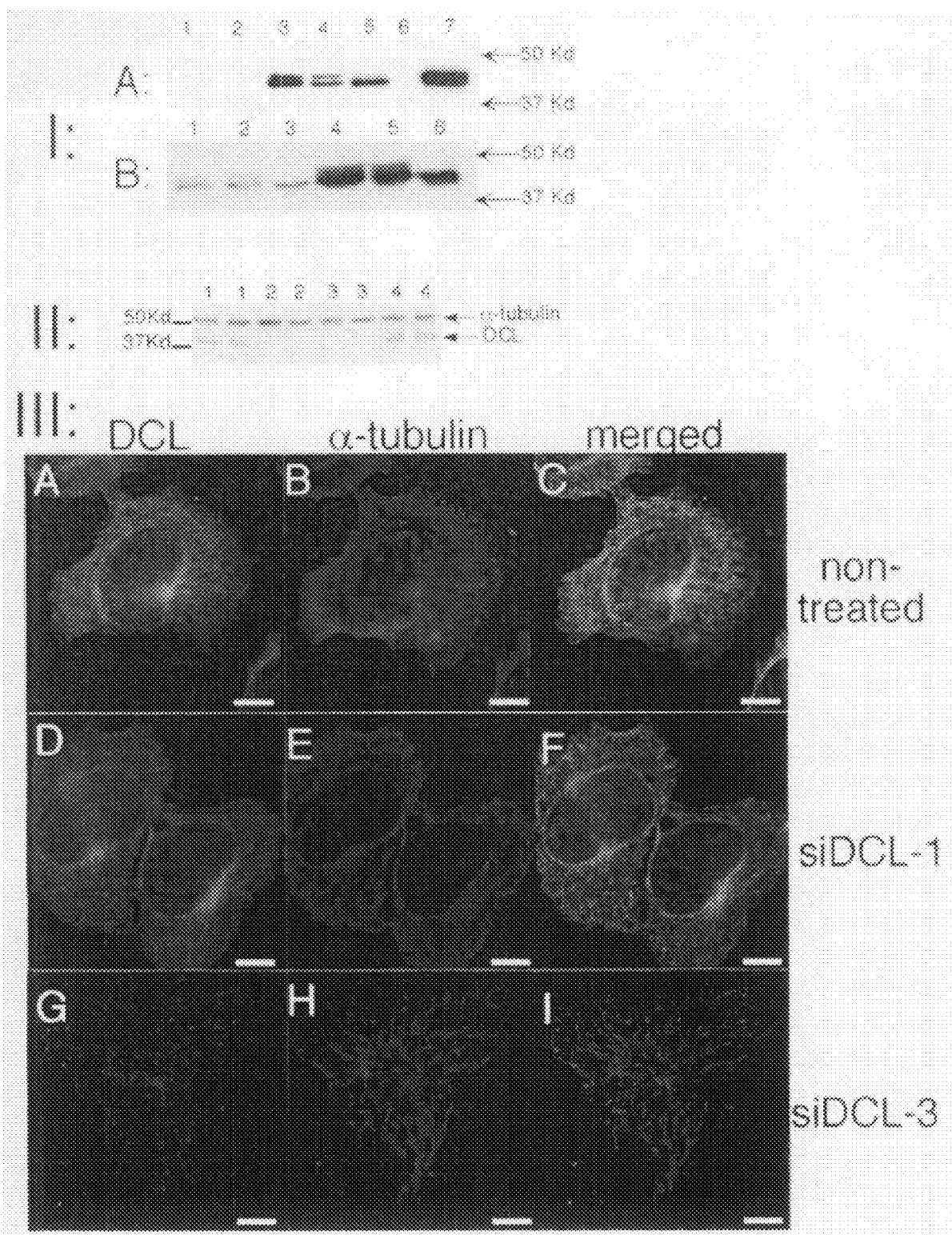
Figure 5:
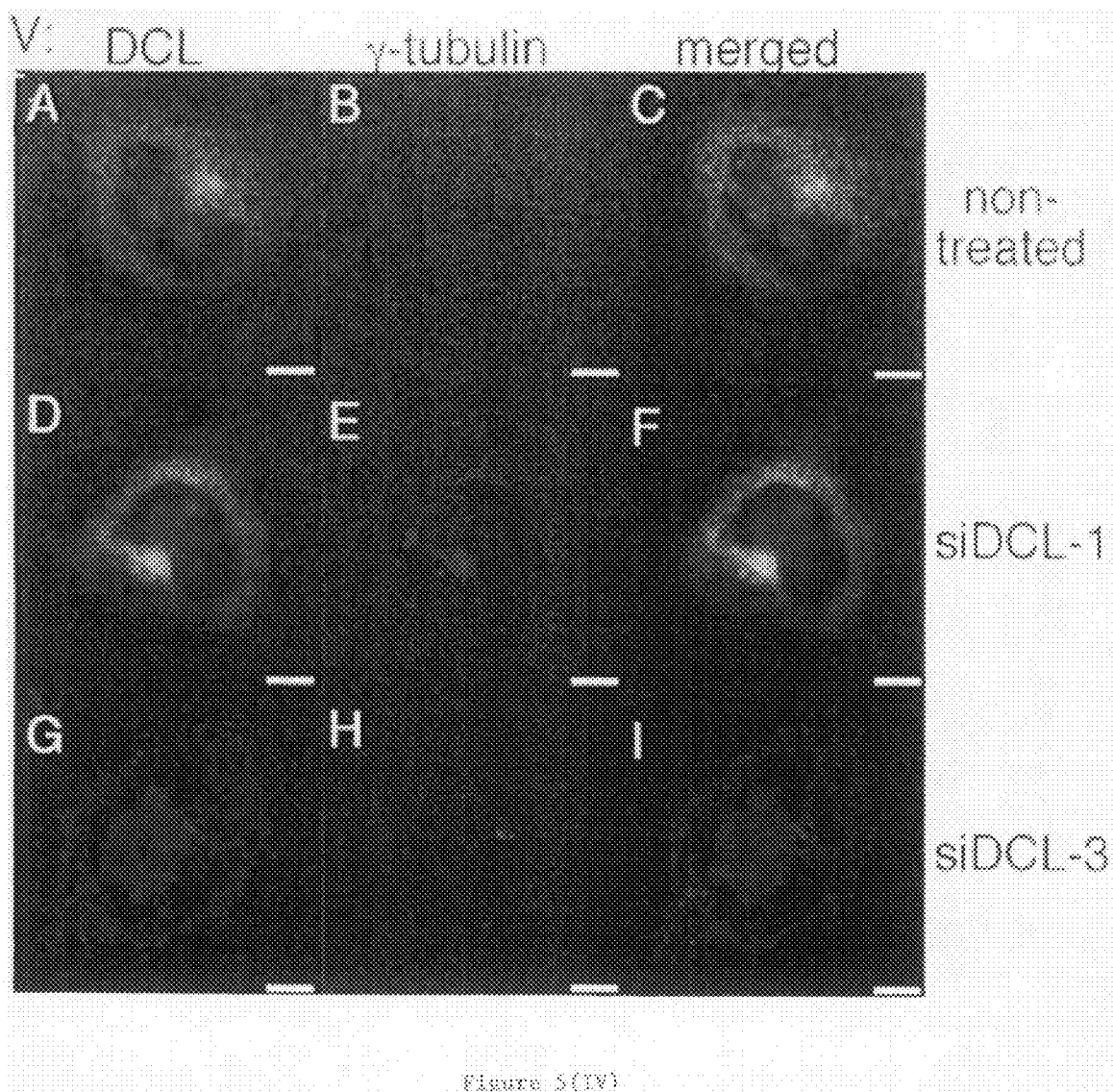

Figure 5.II
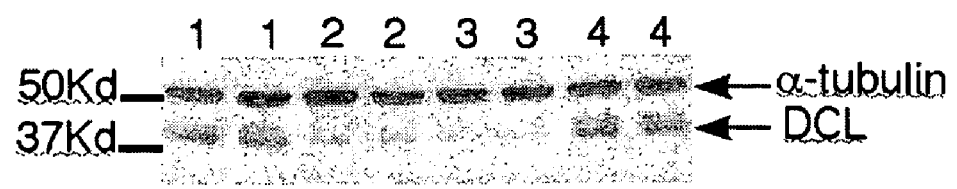

MRNA SPLICE VARIANT OF THE DOUBLECORTIN-LIKE KINASE GENE AND ITS USE IN CANCER DIAGNOSIS AND THERAPY

FIELD OF THE INVENTION

The present invention relates to a novel doublecortin like protein (DCL) and a novel mRNA splice variant encoding it. Provided are mouse and human nucleic acid sequences (RNA and DNA) encoding the novel DCL protein, as well as the mouse and human protein itself and various nucleic acid fragments and variants suitable for therapeutic and diagnostic applications. The invention further relates to methods for modulating DCL protein levels in cancer therapy, especially neuroblastoma therapy, and to diagnostic methods and diagnostic kits.

BACKGROUND OF THE INVENTION

As the most common solid tumor in children, neuroblastoma accounts for 8-10% of all cancers in children (for review see Lee et al., 2003, Urol. Clin. N. Am. 30, 881-890). Annual incidence ranges from 10 to 15 per 100,000 infants, according to population based screening conducted in Canada, Germany and Japan. Neuroblastoma is a heterogeneous disease, with 40% diagnosed in children under 1 year of age who have a very good prognosis, and the rest in older children and young adults who have a poor prognosis despite advanced medical and surgical management. A common treatment for intermediate- and high-risk patients is chemotherapy followed by surgical resection. However, complete eradication of neuroblastoma cells is seldom achieved. Consequently, the majority of these patients undergo relapse, which is often resistant to conventional treatment and rapidly overwhelming. Thus, after induction of the apparent remission by the first-line therapy, new therapeutic strategies are needed to completely eradicate the small number of surviving cells, to prevent relapse (Lee et al., 2003, supra).

Brain development requires the co-ordinated and precise patterning of cell division, migration and differentiation of neuroblasts (Noctor et al., 2001, Nature 409, 714-720; Noctor et al., 2004, Nat. Neuroscience 7, 136-144). A key event in both these processes is the (re)organization and (de)stabilization of the cytoskeleton, which is comprised of microtubules and microtubule-associated proteins (MAPs). A carefully orchestrated interaction of microtubules with several MAPs is required before neuronal migration can occur (reviewed in Feng and Walsh, 2001, Nat. Rev. Neurosci. 2, 408-416). Although the factors involved in neuronal migration are well established, relatively little is known about the genes that control earlier processes, like mitosis and neuroblast proliferation. Such factors very likely involve dynamic regulation of the microtubular and cytoskeletal elements as well (Haydar et al., 2003, Proc. Natl. Acad. Sci. 100, 2890-2895; Kaltschmidt et al., 2000, Nat. Cell Biol. 2, 7-12; Knoblich, 2001, Nat. Rev. Mol. Cell Biol. 2, 11-20).

Recently, several genes involved in cytoskeleton reorganization have been identified that, when disrupted or mutated, cause neuronal migration disorders (reviewed in Feng and Walsh, 2001, supra). One of these genes is doublecortin (DCX) that encodes a 365 AA protein critical for migration of newborn cortical neurons (see WO99/27089). In the human and rodent genome, a related gene, called doublecortin-like kinase (DCLK), is present that has substantial sequence identity with the DCX gene. The human DCLK gene spans more than 250 kb and is subject to extensive alternative splicing, generating multiple transcripts encoding different proteins (Matsumoto et al., 1999, Genomics 56, 179-183). One of the main transcripts, DCLK-long, encodes a DCX domain fused to a kinase-like domain that has amino acid homology with members of the Ca++/Calmodulin dependent protein kinase (CaMK) family. Another transcript, DCLK-short, is mainly expressed in adult brain, lacks the DCX domain and encodes a kinase with CaMK-like properties (Engels et al., 1999, Brain Res. 835, 365-368; Engels et al., 2004, Brain Res. 120, 103-114; Omori et al., 1998, J. Hum. Genet. 43, 169-177; Vreugdenhil et al., 2001, Brain Res. Mol. Brain Res. 94, 67-74). Recent studies suggest important roles for the DCLK gene in calcium-dependent neuronal plasticity and neurodegeneration (Burgess and Reiner, 2001, J. Biol. Chem. 276, 36397-36403; Kruidering et al., 2001, J. Biol. Chem. 276, 38417-38425). DCLK-long is expressed during early development (Omori et al, 1998, supra) and like DCX, is capable of microtubule polymerization (Lin et al., 2000, J. Neurosci. 20, 9152-9161). However, the precise role of the DCLK gene in development of the nervous system is unknown.

Various alternative splice-variants of DCLK have been described and two of these have been found to be differentially expressed and to have different kinase activities (Burgess and Reiner 2002, J. Biol. Chem. 277, 17696-17705). The present inventors cloned and functionally characterized a novel splice variant of the DCLK gene, referred to as doublecortin-like (DCL) herein, and have shown that DCL is a cytoskeleton gene which is associated with mitotic spindles of dividing neuroblasts. In addition, the present inventors have devised novel methods for cancer therapy and diagnosis, especially for neuroblastoma therapy and diagnosis.

Recently, new approaches for treatment of neuroblastoma have been published, involving the use of antisense oligonucleotides targeting two different oncogenes (Pagnan et al., 2000, J. Natl. Cancer Inst. Vol 92, 253-261; Brignole et al. 2003, Cancer Lett. 197, 231-235; Burkhart et al., 2003, J. Natl. Cancer Inst. 95, 1394-1403). The first approach was directed against the c-Myb oncogene (Pagnan et al., 2000, supra). C-Myb gene expression has been reported in several solid tumors of different embryonic origins, including neuroblastoma, where it is linked to cell proliferation and differentiation. It was shown that a phosphorothioate oligodeoxynucleotide complementary to codons 2-9 of human c-Myb mRNA inhibited growth of neuroblastoma cells in vitro. Its inhibitory effect was greatest when it was delivered to the cells in sterically stabilized liposomes coated with a monoclonal antibody (mAb) specific for the neuroectoderma antigen disialoganglioside $GD_2$ (Pagnan et al., 2000, supra). Although pharmaco-kinetic and biodistribution studies after intravenous injection of anti-$GD_2$-targeted liposomes have been performed (Brignole et al., 2003, supra), the effect in an in vivo neuroblastoma model has not been shown so far. Potential toxic side-effects of a c-Myb antisense oligonucleotide should also be considered, since the c-Myb protein plays a fundamental role in the proliferation of normal cells and it has already been shown that a c-Myb antisense oligonucleotide inhibits normal human hematopoiesis in vitro (Gewirtz and Calabretta, 1988, Science 242, 1303-1306).

Another antisense approach was directed against the MYCN(N-myc) oncogene (Burkhart et al., 2003, supra). Amplification of the MYCN gene occurs in only 25 to 30% of neuroblastomas, but is associated with advanced-stage disease, rapid tumor progression and a survival rate of less than 15%. The effect of a phosphorothioate oligodeoxynucleotide complementary to the first five codons of human MYCN mRNA was tested in vivo in a murine model of neuroblastoma. It was shown that continuous delivery of the oligonucleotide for 6 weeks via a subcutaneously implanted microosmotic pump could decrease tumor incidence and tumor mass at the site of the implanted pump (Burkhart et al., 2003, supra). This approach is very local however, and a systemic effect of the oligonucleotide on metastases to distant organ sites remains to be established, in addition to potential toxic side effects on normal cells after systemic delivery. Also, the effect of the oligonucleotide on an already established tumor has not been shown.

The choice of the target gene is crucial for the development of an effective neuroblastoma therapy and diagnosis. As mentioned above, the present inventors have cloned a novel mRNA splice variant of the DCLK gene, encoding the novel DCL protein, and have functionally characterized this splice variant. It was surprisingly found that this splice variant is exclusively expressed in neuroblastomas, while not being detectable in the healthy tissue and cell lines tested. This finding was used to devise novel therapeutic and diagnostic methods.

DEFINITIONS

"Gene silencing" refers herein to a reduction (downregulation) or complete abolishment of target protein production in a cell. Gene silencing may be the result of a reduction of transcription and/or translation of the target gene. The "target gene(s)" is/are the gene(s) which is/are to be silenced. The target gene is usually an endogenous gene, but may in certain circumstances be a transgene. As methods can be used to silence all or several members of a gene family, the term "target gene" may also refer to a gene family which is to be silenced.

The term "gene" refers to the nucleic acid sequence which is transcribed into an mRNA molecule ("transcribed region"), operably linked to various sequence elements necessary for transcription, such as a transcription regulatory sequence, enhancers, 5'leader sequence, coding region and 3'nontranslated sequence. An endogenous gene is a gene found naturally within a cell.

"Sense" refers to the coding strand of a nucleic acid molecule, such as the coding strand of a duplex DNA molecule or an mRNA transcript molecule. "Antisense" refers to the reverse complement strand of the sense strand. An antisense molecule may be an antisense DNA or an antisense RNA, i.e. having an identical nucleic acid sequence as the antisense DNA, with the difference that T (thymine) is replaced by U (uracil).

The term "comprising" is to be interpreted as specifying the presence of the stated parts, steps or components, but does not exclude the presence of one or more additional parts, steps or components. A nucleic acid sequence comprising region X, may thus comprise additional regions, i.e. region X may be embedded in a larger nucleic acid region.

The term "substantially identical", "substantial identity" or "essentially similar" or "essential similarity" means that two peptide or two nucleotide sequences, when optimally aligned, such as by the programs GAP or BESTFIT using default parameters, share at least about 75%, preferably at least about 80% sequence identity, preferably at least about 85 or 90% sequence identity, more preferably at least 95%, 97%, 98% sequence identity or more (e.g., 99%, sequence identity). GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, Proc. Natl. Acad. Science 89, 915-919). It is clear than when RNA sequences are said to be essentially similar or have a certain degree of sequence identity with DNA sequences, thymine (T) in the DNA sequence is considered equal to uracil (U) in the RNA sequence. "Identical" sequences have 100% nucleic acid or amino acid sequence identity when aligned. Also in this case an RNA sequence is 100% identical to a DNA sequence if the only difference between the sequences is that the RNA sequence comprises U instead of T at identical positions. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA. Alternatively percent similarity or identity may be determined by searching against databases such as FASTA, BLAST, etc.

When referring to "sequences" herein or to "sequence fragments", it is understood that molecules with a certain sequence of nucleotides (DNA or RNA) or amino acids are referred to.

"Stringent hybridization conditions" can also be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions. Stringent conditions for DNA-DNA hybridization (Southern blots using a probe of e.g. 100 nt) are for example those which include at least one wash (usually 2) in 0.2×SSC at a temperature of at least 50° C., usually about 55° C., for 20 min, or equivalent conditions.

A "subject" refers herein to a mammalian subject, especially to a human or animal subject.

"Target cell(s)" refers herein to the cells in which DCL protein levels are to be modified (especially reduced) and include any cancer cells in which DCL protein is normally produced, especially neuroblastoma cells. The presence of DCL in target cells can be determined as described elsewhere herein. Below only neuroblastoma therapy and diagnosis is referred to, but it is understood that any reference to neuroblastoma cells can be applied analogously to other types of cancer target cells and that such methods, uses and kits are encompassed herein.

DETAILED DESCRIPTION OF THE INVENTION

The present invention provides novel nucleic acid and protein sequences for use in neuroblastoma therapy and diagnostic methods. The DCL protein was found to be cell-specifically expressed in all neuroblastoma cell lines tested so far (human and mouse cell lines). DCL was found to polymerize and stabilize microtubules and co-localization of endogenous DCL with mitotic spindles in dividing neuroblastoma cells indicates a role of DCL in correct formation of the mitotic spindle in dividing cells. DCL gene silencing in neuroblastoma cell lines resulted in dramatic deformation or even absence of the mitotic spindle and microtubule disassembly.

The invention thus concerns a method for the treatment of neuroblastoma, said method comprising administering to a subject in need thereof a therapeutically active amount of a nucleic acid fragment of SEQ ID NO: 1 or 2, or of a variant of SEQ ID NO: 1 or 2, said nucleic acid fragment being capable of causing a significant reduction of the amount of DCL-protein of SEQ ID NO: 3 or 4.

Also the invention concerns a composition suitable for the treatment of neuroblastoma comprising one or more nucleic acid fragments of SEQ ID NO: 1 or 2, or of a variant of SEQ ID NO: 1 or 2, said nucleic acid fragment being capable of causing a significant reduction of the amount of DCL-protein of SEQ ID NO: 3 or 4 when introduced into neuroblastoma cells and a pharmaceutically and/or physiologically acceptable carrier.

Nucleic Acid and Amino Acid Sequences According to the Invention

The present invention provides novel nucleic acid sequences, SEQ ID NO: 1 (mouse dcl mRNA and cDNA) and SEQ ID NO: 2 (human dcl mRNA and cDNA), which encode the proteins SEQ ID NO: 3 (mouse DCL) and SEQ ID NO: 4 (human DCL). The dcl mRNA sequences of SEQ ID NO: 1 and 2 are novel splice variants of the mouse and human DCLK gene. The splice variants comprise exon 1 to exon 8 (partially, up to a stop codon), wherein exon 1 is non-coding. In both sequences, exon 6 of the DCLK gene is absent. In the mouse mRNA sequence, the translation start codon is found at nucleotides 189-191, while the translation stop codon is found at nucleotides 1275-1277. Exon 2 starts at nt 169, exon 3 starts at nt 565, exon 4 starts at nt 912, exon 5 starts at nt 1012, exon 7 starts at nt 1129 and exon 8 starts at nt 1224. In the human mRNA sequence, the translation start codon is found at nucleotides 213-215, while the translation stop codon is found at nucleotides 1302-1304. Exon 2 starts at nt 194, exon 3 starts at nt 589, exon 4 starts at nt 936, exon 5 starts at nt 1036, exon 7 starts at nt 1153 and exon 8 starts at nt 1248. The mouse and human DCL proteins are very similar in their amino acid sequence and both have a molecular weight of about 40 kDa. The mouse DCL protein comprises 362 amino acids, while the human DCL protein comprises 363 amino acids. Amino acid sequence identity is about 98%, as only 4 amino acid differences are present. These are at amino acid 172, which is G in the mouse sequence and S in the human sequence, at position 290 (A in the mouse sequence vs. S in the human sequence), at position 294 (G in the mouse sequence vs. S in the human sequence) and the V at position 359 of the human sequence is absent from the mouse sequence. Due to the high sequence similarity also at the cDNA/mRNA level (which is about 90% for the coding region), either nucleic acid sequence (SEQ ID NO: 1 or 2), or fragments or variants thereof, may be used in gene silencing approaches of target cells, especially of human neuroblastoma cells.

It is understood that when reference is made herein to an RNA or mRNA molecule, while the sequence listing depicts a DNA sequence, the RNA molecule is identical to the DNA sequence with the difference that T (thymine) is replaced by U (uracil).

Apart from the complete nucleic acid sequences of dcl (SEQ ID NO: 1 and 2), also sense and/or anti-sense fragments of SEQ ID NO: 1 and 2 are provided, which are suitable for use in gene silencing methods having dcl as target gene. The fragment(s) must thus be functional when used in any one of the gene silencing methods described below, and in particular they cause a significant reduction of the production of the DCL protein of SEQ ID NO: 3 or 4 when present in neuroblastoma cells. A "significant reduction in the production of SEQ ID NO: 3 or 4" refers to a reduction of the DCL-protein of at least 50%, 60%, 70%, preferably at least 80%, 90% or 100% in neuroblastoma cells comprising the sense and/or antisense fragment of SEQ ID NO: 1 and/or 2, compared to the DCL-protein level found in neuroblastoma cells into which no sense and/or antisense fragments of SEQ ID NO: 1 and/or 2 were introduced. In addition, the introduction of the sense and/or antisense fragment of SEQ ID NO: 1 and/or 2 causes, by significantly reducing or abolishing DCL-protein production in the cell, a phenotypic change to the cell. In particular, microtubule disassembly and deformation of the mitotic spindle results and proliferation of neuroblastoma cells is significantly reduced. A "significant reduction of neuroblastoma cell proliferation" refers to a reduction or complete inhibition in growth (cell division) of neuroblastoma cells comprising the sense and/or antisense fragments of SEQ ID NO: 1 and/or 2. A skilled person can easily test, using the methods described herein, whether a sense and/or antisense fragment of SEQ ID NO: 1 and/or 2 has the ability to cause the desired effect. The easiest method to test this is to introduce the sense and/or antisense fragments into neuroblastoma cell lines cultured in vitro and analyze dcl mRNA and/or DCL-protein levels and/or phenotypic changes and/or neuroblastoma cell proliferation in those cell, compared to control cells. The in vitro effect reflects the suitability of the sense and/or antisense fragments to be used to make a composition for the treatment of neuroblastoma.

In principle, a (sense and/or antisense) fragment of SEQ ID NO: 1 and/or 2 may be any part of SEQ ID NO: 1 or 2 comprising at least 10, 12, 14, 16, 18, 20, 22, 25, 30, 50, 100, 200, 500, 1000 or more consecutive nucleotides of SEQ ID NO: 1 or 2, or its complement or its reverse complement. The sense and/or antisense fragment may be an RNA fragment or a DNA fragment. Further, the fragment may be single stranded or double stranded (duplex). The nucleic acid fragment may also be 100% identical to part of the non-coding region of SEQ ID NO: 1 or 2 (e.g. to a region of nucleotides 1-188 of SEQ ID NO: 1 or nucleotides 1-212 of SEQ ID NO: 2), or to part of the coding region (nucleotide 189 to 1274 of SEQ ID NO: 1 or nucleotide 213 to 1301 of SEQ ID NO: 2) or to a region which is partly non-coding and partly coding (such as intron-exon boundaries or exon 1). A nucleic acid fragment may be made de novo by chemical synthesis, using for example an oligonucleotide synthesizer as supplied e.g. by Applied Biosystems Inc. (Fosters, Calif., USA), or may be cloned using standard molecular biology methods, such as described in Sambrook et al. (1989) and Sambrook and Russell (2001). The nucleic acid fragments according to the invention may be used for various purposes, such as: as PCR primers, as probes for nucleic acid hybridization, as DNA or RNA oligonucleotides to be delivered to target cells or as siRNAs (small interfering RNAs) to be delivered to or to be expressed in target cells. Because different gene silencing methods make use of different sense and/or antisense nucleic acid fragments, these will, without limiting the scope of the present invention, be described in detail below.

In addition, variants of SEQ ID NO: 1 and 2, their complement or reverse complement, as described above, are provided. "Variants" are not 100% identical in nucleic acid sequence to SEQ ID NO: 1 or 2 (or their complement or reverse complement), but are "essentially similar" in their nucleic acid sequence. "Variants of SEQ ID NO: 1 or 2" include nucleic acid sequences which, due to the degeneracy of the genetic code, also encode the amino acids of SEQ ID NO: 3 or 4, or fragments thereof. Variants of SEQ ID NO: 1 or 2, their complement, reverse complement encompasses also SEQ ID NO: 1 or 2 which differs from SEQ ID NO: 1 or 2 through substitutions, deletions and/or replacement of one or more nucleotides. "Variants of SEQ ID NO: 1 and 2" also includes sequences comprising or consisting of mimics of nucleotides such as PNA's (Peptide Nucleic Acid), LNA's (Locked Nucleic Acid) and the like or comprising morpholino, 2'-O-methyl RNA or 2'-O-allyl RNA.

Variant nucleic acid sequences may, for example, be made de novo by chemical synthesis, generated by mutagenesis or gene shuffling methods or isolated from natural sources, using for example PCR technology or nucleic acid hybridization. A variant of SEQ ID NO: 1 or 2 can also be defined as a nucleic acid sequence which is "essentially similar" (as defined above) to SEQ ID NO: 1 or 2, their complement or reverse complement. Especially, variants which have at least 75%, 80%, 85%, 90%, 95% or more sequence identity with SEQ ID NO: 1 or 2 over the entire length of the sequence are encompassed herein. In one embodiment of the invention sense and/or antisense fragments of nucleic acid sequences which are essentially similar to SEQ ID NO: 1 or 2 are provided. As described for the fragments of SEQ ID NO: 1 or 2, the fragments of variants of SEQ ID NO: 1 or 2 have the ability to significantly reduce the cellular levels of the DCL-protein when introduced in suitable amounts into neuroblastoma cells. Functionally, these variant fragments must therefore be equivalent to the sense and/or antisense fragments described, and a skilled person can test the functionality of such fragments in the same way as described.

Also provided are the isolated proteins of SEQ ID NO: 3 and SEQ ID NO: 4, as well as fragments and variants thereof. The DCL proteins (or fragments or variants thereof) according to the invention may for example be used to raise antibodies, such as monoclonal or polyclonal antibodies, which may then be used in various DCL detection methods, diagnostic or therapeutic methods, or kits. Such antibodies and their use in DCL detection methods are an embodiment of the invention. Alternatively, epitopes, which elicit an immune response may be identified within the proteins. The DCL proteins, fragments or variants thereof may be made synthetically, may be purified from natural sources or may be expressed in recombinant cells or cell cultures. A DCL protein fragment may be any fragment of SEQ ID NO: 3 or SEQ ID NO: 4 comprising 20, 50, 100, 200, or more consecutive amino acids identical or essentially similar to the corresponding part of SEQ ID NO: 3 or 4. DCL protein variants include amino acid sequences which have substantial sequence identity to SEQ ID NO: 3 or 4, for example amino acid sequences which differ from SEQ ID NO: 3 or 4 by 1, 2, 3, 4, 5 or more amino acid substitutions, deletions or insertions. Variants also include proteins comprising peptide backbone modifications or amino acid mimetics, such as non-protein amino acids (e.g. β-, γ-, δ-amino acids, β-, γ-, δ-imino acids) or derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) Ann. Repts. Med. Chem. 24:243-252.

Methods According to the Invention

In one embodiment, the invention provides methods for silencing dcl gene(s) in target cells or tissues, especially in neuroblastoma cells. These methods have in common that one or more sense and/or antisense nucleic acid fragments of SEQ ID NO: 1 or 2 or fragments of variants of SEQ ID NO: 1 or 2 (as described above) is/are delivered to the target cell(s) (neuroblastoma cells) and is/are introduced into the target cell(s), whereby the introduction into the target cell(s) results in silencing of the endogenous dcl gene(s) (the target gene), and in particular results in a significant reduction of DCL-protein and neuroblastoma cell proliferation.

Various gene silencing methods are known in the art. Generally, RNA or DNA with sequence homology to an endogenous target gene is introduced into a cell with the aim of interfering with transcription and/or translation of the endogenous target gene. Production of the target protein is thereby significantly reduced or preferably completely abolished. Known gene silencing methods include antisense RNA expression (see e.g. EP140308B1), co-suppression (sense RNA expression, see e.g. EP0465572B1), delivery or expression of small interfering RNAs (siRNA) into cells (see WO03/070969, Fire et al. 1998, Nature 391, 806-811, WO03/099298, EP1068311, Zamore et al. 2000, Cell 101: 25-33, Elbashir et al. 2001, Genes and Development 15:188-200; Sioud 2004, Trends Pharmacol. Sci. 25:22-28) and antisense oligonucleotide delivery into cells (see e.g. WO03/008543, Pagnan et al. 2000 supra, Burkhard et al. 2003, supra). See also Yen and Gerwitz (2000, Stem Cells 18:307-319) for a review of gene silencing approaches.

In addition, various methods for delivering the nucleic acid molecules to the target cells exist and may be used herein, such as (cationic) liposome delivery (Pagnan et al. 2000, supra), cationic porphyrins, fusogenic peptides (Gait, 2003, Cell. Mol. Life Sci. 60: 844-853) or artificial virosomes (for review see Lysik and Wu-Pong, 2003, J. Pharm. Sci. 92:1559-1573; Seksek and Bolard, 2004, Methods Mol. Biol. 252: 545-568).

The cloning and characterization of the mouse and human DCL splice variant enables the use of any of the known gene silencing methods for significantly reducing the DCL protein level (or for completely abolishing DCL protein production) in mouse or human neuroblastoma cells in vitro (in cell or tissue culture) or in vivo. Especially, the phenotypic effect of DCL silencing is seen as a deformation of the mitotic spindle in dividing neuroblastoma cells and/or a significant reduction or complete inhibition of proliferation of neuroblastoma cells in vivo or in vitro.

In one embodiment the use of one or more sense and/or antisense nucleic acid fragments of SEQ ID NO: 1 or 2, or fragments of variants of SEQ ID NO: 1 or 2, for the preparation of a composition for the significant reduction of DCL protein levels in neuroblastoma cells, and for the treatment of neuroblastoma, is provided. In particular, administration of the composition in suitable amounts and at suitable time intervals results in a reduction or complete inhibition of neuroblastoma cell proliferation.

In another embodiment a method for in vitro treatment of neuroblastoma cells is provided. This method can be used to test the functionality of nucleic acid fragments and compositions comprising these. The method comprises a) establishment of cell cultures of neuroblastoma cell lines, b) the treatment of the cells with nucleic acid fragments or compositions comprising the nucleic acid fragments according to the invention and c) the analysis of phenotypic changes of the neuroblastoma cells compared to control cells (cell proliferation, microtubule disassembly, etc., using visual assessment, microscopy, etc.) and/or the molecular analysis of the cells (analysing dcl transcript levels, DCL protein levels, etc., using e.g. PCR, hybridization, chemiluminescent detection methods, etc.).

Non-limiting examples of sense and/or antisense DNA or RNA molecules with sequence identity or essential sequence similarity to SEQ ID NO: 1 and/or 2, suitable for dcl gene silencing, are the following:

1. Small Interfering RNAs (siRNA)

Small interfering RNAs consist of double stranded RNA (dsRNA) of 18, 19, 20, 21, 22, 23, 24, 25, 30, or more contiguous nucleotides of the SEQ ID NO: 1 or 2. Such dsRNA molecules can easily be made synthetically by synthesizing short single RNA oligonucleotides of the desired sequence and annealing these subsequently (see Examples). Preferably additional one, two or three nucleotides are present as 3'overhangs, most preferably two thymine nucleotides or thymidine deoxynucleotides (3'-end TT). These dsRNAs comprise both sense and antisense RNA. Non-limiting examples are the following:

```
(siDCL-2)
5'-CAAGAAGACGGCUCACUCCTT-3'      (SEQ ID NO: 5)

3'-TTGUUCUUCUGCCGAGUGAGG-5'      (SEQ ID NO: 6)

(hu-siDCL-2)
5'-CAAGAAAACGGCUCAUUCCTT-3'      (SEQ ID NO: 7)

3'-TTGUUCUUUUGCCGAGUAAGG-5'      (SEQ ID NO: 8)

(siDCL-3)
5'-GAAAGCCAAGAAGGUUCGATT-3'      (SEQ ID NO: 9)

3'-TTCUUUCGGUUCUUCCAAGCT-5'      (SEQ ID NO: 10)

(hu-siDCL-3)
5'-GAAGGCCAAGAAAGUUCGUTT-3'      (SEQ ID NO: 11)

3'-TTCUUCCGGUUCUUUCAAGCA-5'      (SEQ ID NO: 12)
```

As mentioned above, any other fragment of SEQ ID NO: 1 or 2, or of a variant of SEQ ID NO: 1 or 2, may suitably be used to construct siRNAs. siRNA molecules may also comprise labels, such as fluorescent or radioactive labels, for monitoring and detection.

Conveniently, siRNAs may also be expressed from a DNA vector. Such DNA vectors may comprise additional nucleotides between the sense and the antisense fragment, resulting in stem-loop structure, following folding of the RNA transcript. Instead of delivery and introduction of the siRNA molecules into neuroblastoma cells such DNA vectors may be transiently or stably introduced into the target cells, so that the siRNA is transcribed within the target cells. For example, vectors for gene delivery, such as those developed for gene therapy, may be used to deliver DNA into neuroblastoma cells, from which sense and/or antisense fragments of SEQ ID NO: 1 or 2 or of variants of SEQ ID NO: 1 or 2 are transcribed. Examples are recombinant adeno-associated viral vectors (AAV), as described in Hirata et al., 2000 (J. of Virology 74:4612-4620), Pan et al. (J. of Virology 1999, Vol 73, 4: 3410-3417), Ghivizanni et al. (2000, Drug Discov. Today 6:259-267) or WO99/61601.

A skilled person can easily test whether a siRNA molecule is suitable for, and effective in, dcl gene silencing, by for example delivering the molecule into neuroblastoma cell lines and subsequently assessing dcl mRNA and/or DCL protein levels produced by the cells comprising the siRNA molecule(s), using known methods, such as RT-PCR, Northern Blotting, nuclease protection assays, Western Blotting, ELISA assays and the like. Suitable neuroblastoma cell lines are for example human SHSY5, mouse N1E-115, mouse NS20Y or mouse neuroblastoma/rat glioma hybrid NG108 lines, or others. Alternatively, phenotypic effects of dcl gene silencing, such as mitotic spindle deformation, can be assessed, as described in the Examples using, for example immunocytochemical staining or immunofluorescence. Anti-DCL-antibodies can be generated by a skilled person, e.g. as described in the Examples, or an existing antibody (Kruidering et al. 2001, supra), which was herein found to have a high specificity for DCL, may be used.

DCL protein levels are preferably reduced by at least about 50%, 60%, 70%, 80%, 90% or 100% following introduction of siRNA molecules into neuroblastoma cells, compared to cells without the siRNA molecules or compared to cells comprising negative control siRNA molecules, such as siDCL-1 described in the Examples.

2) Antisense RNA Oligonucleotides

Antisense RNA oligonucleotides consist of about 12, 14, 16, 18, 20, 22, 25, 30, or more contiguous nucleotides of the reverse complement sequence of SEQ ID NO: 1 or 2. Such RNA oligonucleotides can easily be made synthetically or transcribed from a DNA vector.

Backbone modifications, such as the use of phosphorothioate oligodeoxynucleotides, may be used to increase the oligonucleotide stability. Other modifications, such as to the 2'sugar moiety, e.g. with O-methyl, fluoro, O-propyl, O-allyl or other groups may also improve stability.

Non-limiting examples of suitable antisense RNA oligonucleotides are:

```
(DCLex2C) (2'O-methyl RNA phosphorothioate)
5'-GCUGGGCAGGCCAUUCACAC-3'                         (SEQ ID NO: 13)

(hu-DCLex2C) (2'O-methyl RNA phosphorothioate)
5'-GCUCGGCAGGCCGUUCACCC-3'                         (SEQ ID NO: 14)

(DCLex2D) (2'O-methyl RNA phosphorothioate)
5'-CUUCUCGGAGCUGAGUGUCU-3'                         (SEQ ID NO: 15)

(hu-DCLex2D) (2'O-methyl RNA phosphorothioate)
5'-CUUCUCGGAGCUGAGCGUCU-3'                         (SEQ ID NO: 16)
```

As for the siRNA molecules, a skilled person can easily make other suitable antisense RNA oligonucleotides and test their dcl-gene silencing efficiency as described above. Instead of using contiguous stretches, which match the reverse complement SEQ ID NO: 1 or 2 to 100%, sequences which are essentially similar to the reverse complement of SEQ ID NO: 1 or 2 may be used, for example by adding, replacing or deleting 1, 2 or 3 nucleotides.

Encompassed are also DNA molecules, in particular DNA vectors capable of producing antisense RNA oligonucleotides as RNA transcripts or as part of a transcript. Such vectors can be used to produce the antisense RNA oligonucleotides when the vector is present in suitable cell lines. DNA vectors (e.g. AAV vectors, see above) may also be delivered into neuroblastoma cells in vivo in order to silence endogenous dcl-gene expression. Thus, instead of delivering antisense RNA oligonucleotides, DNA vectors may be delivered to the neuroblastoma cells and prevent or reduce neuroblastoma cell proliferation.

DCL protein levels are preferably reduced by at least about 50%, 60%, 70%, 80%, 90% or 100% following introduction of antisense RNA oligonucleotides into neuroblastoma cells, compared to cells without the antisense RNA oligonucleotides or compared to cells comprising negative control antisense RNA oligonucleotides (i.e. without effect on DCL protein levels).

3) Antisense DNA Oligonucleotides

Antisense DNA oligonucleotides consist of about 12, 14, 16, 18, 20, 22, 25, 30, or more contiguous nucleotides of the reverse complement of SEQ ID NO: 1 or 2. Such DNA oligonucleotides can easily be made synthetically.

Backbone modifications, such as the use of phosphorothioate oligodeoxynucleotides, may be used to increase the oligonucleotide stability. Other modifications, such as to the 2'sugar moiety, e.g. with O-methyl, fluoro, O-propyl, O-allyl or other groups may also improve stability.

Non-limiting examples of suitable antisense DNA oligonucleotides are:

```
(DCLex2A) (DNA phosphorothioate)
5'-GCTGGGCAGGCCATTCACAC-3'              (SEQ ID
                                         NO: 17)

(hu-DCLex2A) (DNA phosphorothioate)
5'-GCTCGGCAGGCCGTTCACCC-3'              (SEQ ID
                                         NO: 18)

(DCLex2B) (DNA phosphorothioate)
5'-CTTCTCGGAGCTGAGTGTCT-3'              (SEQ ID
                                         NO: 19)

(hu-DCLex2B) (DNA phosphorothioate)
5'-CTTCTCGGAGCTGAGCGTCT-3'              (SEQ ID
                                         NO: 20)
```

As for the siRNA molecules and antisense RNA oligonucleotides, a skilled person can easily make other suitable antisense DNA oligonucleotides and test their dcl-gene silencing efficiency as described above.

Instead of using contiguous stretches, which match the reverse complement of SEQ ID NO: 1 or 2 to 100%, sequences which are essentially similar to the reverse complement of SEQ ID NO: 1 or 2 may be used, for example by adding, replacing or deleting 1, 2 or 3, or more nucleotides.

DCL protein levels are preferably reduced by at least about 50%, 60%, 70%, 80%, 90% or 100% following introduction of antisense DNA oligonucleotides into neuroblastoma cells, compared to cells without the antisense DNA oligonucleotides or compared to cells comprising negative control antisense DNA oligonucleotides (i.e. without effect on DCL protein levels).

It is understood, that delivery of mixtures of siRNA molecules, antisense RNA oligonucleotides and/or antisense DNA oligonucleotides may also be used for dcl specific silencing.

The compositions according to the invention thus comprise a suitable amount of a sense and/or antisense fragment of SEQ ID NO: 1 or 2 or of a sequence essentially similar to SEQ ID NO: 1 or 2 and a physiologically acceptable carrier. When the compositions are used for introduction into neuroblastoma cell cultures in vitro, the composition may also comprise a targeting compound, although the presence of a targeting compound is not required, as the molecules may be introduced simply by transfection using for example transfection kits available (e.g. Superfect, Qiagen, Velancia, Calif.), electroporation, liposome mediated transfection, and the like. A "targeting compound" refers to a compound or molecule which is able to transport the nucleic acid fragments in vivo to the target neuroblastoma cells, i.e. it has cell-targeting capabilities.

A "suitable amount" or a "therapeutically effective amount" refers to an amount which, when present in a neuroblastoma cell, is able to cause DCL protein levels to be significantly reduced or abolished and to cause neuroblastoma cell proliferation to be significantly reduced or inhibited completely. A suitable amount can be easily determined by a skilled person without undue experimentation, as described. Suitable amounts of the sense and/or antisense molecules (siRNA, antisense RNA or DNA oligonucleotides) range for example from 0,05 µmol to 5 µmol per ml and is infused at 1 to 100 ml per kg body weight.

Compositions which are to be administered to a subject, rather than to neuroblastoma cell cultures, comprise a therapeutically effective amount of the nucleic acid molecules of the invention and in addition one or more targeting compounds. Such targeting compounds may, for example, be immunoliposomes, such as described by Pagnan et al. (2000, supra) or by Patorino et al. (Clin Cancer Res. 2003, 9(12): 4595-605). Immunoliposomes comprise cell surface-directed antibodies on their exterior. For example, monoclonal antibodies raised against antigens of neuroblastoma cells, such as the disialoganglioside $GD_2$ antigen, may be used to target the liposomes to neuroblastoma cells. Clearly, other neuroblastoma cell antigens may be used to raise cell specific antibodies. The nucleic acid molecules are encapsulated in the immunoliposomes using known methods and the monoclonal antibodies are covalently coupled to the exterior of the liposomes (see e.g. p254 of Pagnan et al. 2000, supra). The binding of the liposomes to neuroblastoma cells and the uptake of the nucleic acid molecules by the neuroblastoma cells can be assessed in vitro using known methods, as described in Pagnan et al. (2000). Similarly, phenotypic effects and/or molecular effects of the intracellular presence of the nucleic acids can be assessed.

Other targeting compounds may be antibodies as such, for example monoclonal antibodies raised against a neuroblastoma cell surface antigen conjugated to the nucleic acid molecules. For example an anti-transferrin-receptor antibody may be used, such as the chimeric rat/mouse monoclonal antibody ch17217 which has been shown to target cytokines to neuroblastoma tumor cells in mice (Dreier et al., 1998, Bioconj. Chem. 9: 482-489). Such methods are well known in the art, see e.g. Guillemard and Saragovi (Oncogene, Advanced online publication, published 22 Mar. 2004, Prodrug chemotherapeutics bypass p-glycoprotein resistance and kill tumors in vivo with high efficacy and target-dependent selectivity).

Similarly, the nucleic acid molecules according to the invention may be conjugated to natural or synthetic ligands, or ligand mimetics, which bind to the target cell surface receptors (e.g. neuroblastoma cell surface receptors) and which result in the endocytosis of the nucleic acid molecules. An example of such a ligand is for example transferrin. It has been shown that intravenous injection of transferrin-PEG-PEI/DNA complexes resulted in gene transfer to subcutaneous Neuro2a neuroblastoma tumors in mice (Ogris et al., 2003, J. Controlled Release 91: 173-181).

The therapeutic composition may further comprise various other components, such as but not limited to water, saline, glycerol or ethanol. Additional pharmaceutically acceptable auxiliary substances may be present, such as emulsifiers, wetting agents, buffers, tonicity adjusting agents, stabilizers and the like, for example, sodium acetate, sodium lactate, sodium chloride, potassium chloride, calcium chloride, sorbitan monolaurate, and triethanolamine oleate. Other biologically effective molecules may be present, such as nucleotide molecules which silence other gene targets (e.g. c-Myb), markers or marker genes (e.g. luciferase), ligands, antibodies, drugs, etc.

The therapeutic compositions may be administered locally, e.g. by injection, preferably into the target tissue, or systemically, e.g. by dropwise infusion of a parenteral fluid or a subcutaneous slow release device.

Injectable delivery systems include solutions, suspensions, gels, microspheres and polymeric injectables, and can comprise excipients such as solubility-altering agents (e.g. ethanol, propylene glycol and sucrose) and polymers (e.g. polycaprylactones, and PLGA's). Further guidance regarding formulations that are suitable for various types of administration can be found in *Remington's Pharmaceutical Sciences*, Mace Publishing Company, Philadelphia, Pa., 17th ed. (1985).

In one embodiment the compositions according to the invention are used to complement other neuroblastoma therapies, such as chemotherapy, radiation therapy, surgery and/or bone marrow transplantation. Thus, either before, at the same time and/or shortly after one or more conventional treatments, the compositions are administered to the subject, preferably weekly, more preferably monthly, in effective amounts. Any neuroblastoma cells, which are not effectively removed or eradicated by the other therapy are thus prevented from proliferating by dcl silencing. This treatment reduces the risk of spread of neuroblastoma cells to other parts of the body (metastasis formation) and prevents or at least delays relapses, i.e. the recurrence of the (primary) neuroblastoma. DCL silencing has as advantage over chemotherapy or surgery that it has a low toxicity towards normal tissue and a high specificity for neuroblastoma cells. It is therefore likely that undesirable side effects are absent or minimal.

In another embodiment a method for treatment of a subject is provided, whereby no other neuroblastoma therapies (e.g. chemotherapy, surgery, etc.) are carried out. The method comprises a) establishing a diagnosis of neuroblastoma, and b) administering a suitable amount of a composition according to the invention, and c) monitoring at various intervals (follow up treatment).

Step a), diagnosis, can, for example, be established using the diagnostic method and kits described below. Alternatively, neuroblastoma diagnosis may be established using conventional methods, such as CT or CAT scans, MRI scans, mIBG scan (meta-iodobenzylguanidine), X-rays, biopsies or analysis of catecholamines or its metabolites in urine or blood plasma samples (e.g. dopamine, homovanillic acid, r vanillylmandelic acid). Step b) is described elsewhere herein. Step c) may involve various follow up tests, such as the diagnostic test described below, blood or urine tests, CT scans, MRI scan, etc. The purpose of the follow up monitoring is to ensure that the tumor cells are completely eradicated and do not recur. If this is not the case, new treatment needs to be started.

In a further embodiment diagnostic methods and diagnostic kits are provided which are useful for selective screening of early stage neuroblastoma occurrence in subjects. Subjects may already have tested positive in one or more other neuroblastoma tests, in which case the present test may confirm earlier diagnosis. Alternatively, they may not have been diagnosed with neuroblastoma yet, but they may show symptoms which could be caused by neuroblastoma. Depending on the tumor location, symptoms may vary greatly, such as loss of appetite, tiredness, breathing or swallowing difficulties, swollen abdomen, constipation, weakness/unsteadiness in the legs, etc. Alternatively, high risk subjects not showing any symptoms yet may be prophylactically tested at regular intervals using the diagnostic method according to the invention to ensure early diagnosis, which greatly increases the chances of eradication of the neuroblastoma cells. The ex vivo diagnostic methods comprise taking a blood sample from a subject and detecting the presence or absence of free neuroblastoma cells in the serum. Alternatively, the ex vivo diagnostic method may be carried out on a biopsy sample of the (presumed) tumor tissue. As the DCL protein and the dcl mRNA are specific for neuroblastoma cells, the presence of the cells can be detected, and optionally quantified, by analysing the presence of dcl mRNA and/or DCL protein in the sample. This can be done using methods known in the art, such as (quantitative) RT-PCR using dcl-specific or degenerate primers, other PCR methods, such as for example specific amplification of regions of the dcl gene, DNA-arrays, DNA probes for hybridization, or methods which detect the DCL protein, such as Enzyme-linked immunosorbent assays (ELISA) or Western blotting using DCL-specific antibodies (e.g. monoclonal or polyclonal antibodies). In one embodiment the diagnostic method and kit according to the invention comprises the monoclonal antibody anti-DCLK (also referred to as anti-CaMLK in Kruidering et al. 2001, supra), which recognizes and binds human and/or mouse DCL protein (detectable as having a molecular weight of about 40 kDa) according to the invention. Although anti-DCLK also recognizes other splice variants, such as DCLK-short (i.e. cpg16) and CARP, the spatio-temporal separation of DCL from cpg16 and CARP expression, and the differences in molecular weight, can be used to easily minimize/avoid false positives. Clearly, other DCL-specific monoclonal antibodies may be generated and used.

Also, primers or probes specific for exon 8 RNA (present in DCL RNA but absent in DCLK-short RNA) may be used in RNA detection methods. As controls, for example primers or probes which bind to (hybridize with) exon 6 RNA of DCLK-short (i.e. cpg16) and CARP, or to exon 9 to 20 of DCLK may be employed, which are absent in DCL RNA.

Primer pairs, probes and antibodies which specifically detect (e.g. by sequence specific amplification, by sequence specific hybridization or by specific binding) the RNA or DNA of SEQ ID NO: 2 or the protein of SEQ ID NO: 4 can be made by a skilled person using standard molecular biology methods, as found in references to standard textbooks below. Primer pairs and probes can be made on the basis of SEQ ID NO: 2. Monoclonal or polyclonal antibodies specific for DCL-protein can be raised as known in the art.

The diagnostic method comprises the steps of a) analyzing a blood sample of a subject for the presence or absence of SEQ ID NO: 2 RNA or DNA and/or for the presence or absence of DCL protein of SEQ ID NO: 4 and b) optionally quantifying the amount of SEQ ID NO: 2 and/or SEQ ID NO: 4 present. A quantification may allow a direct correlation to the number of neuroblastoma cells present, which in turn may indicate the severity of the neuroblastoma development and spread.

Also provided are ex vivo diagnostic kits for carrying out the method above. A diagnostic kit may, therefore, comprise primers, probes and/or antibodies, and other reagents (buffers, labels, etc.), suitable for dcl gene, dcl mRNA and/or DCL protein detection and optionally quantification. In addition, kits comprise instructions and protocols how to use the reagents (e.g. immunodetection reagents) and control samples, for example isolated DCL-protein or dcl DNA.

The following non-limiting examples illustrate the identification, isolation and characterization of the novel DCL splice variant. Unless stated otherwise, the practice of the invention will employ standard conventional methods of molecular biology, virology, microbiology or biochemistry. Such techniques are described in Sambrook and Russell (2001) *Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and in Volumes I and II of Brown (1998) *Molecular Biology LabFax*, Second Edition, Academic Press (UK), *Oligonucleotide Synthesis* (N. Gait editor), *Nucleic Acid Hybridization* (Hames and Higgins, eds.), "*Enzyme immunohistochemistry*" in Practice and Theory of Enzyme Immunoassays, P. Tijssen (Elsevier 1985). Standard materials and methods for PCR can be found in Dieffenbach and Dveksler (1995) *PCR Primer: A Laboratory Manual*, Cold Spring Harbor Labroatory Press, and in McPherson et al (2000) *PCR Basics: From Background to Bench*, first edition, Springer Verlag Germany. Methods for making monoclonal or polyclonal antibodies are for example described in Harlow and Lane, *Using Antibodies: A laboratory Manual*, New York: Cold Spring Harbor Laboratory Press, 1998, and in Leddell and Cryer "*A Practical Guide to Monoclonal Antibodies*", Wiley and Sons 1991. All above references are incorporated herein by reference.

Throughout the description and Examples reference to the following sequences is made:

SEQ ID NO 1: cDNA sequence of mouse dcl
SEQ ID NO 2: cDNA sequence of human dcl
SEQ ID NO 3: amino acid sequence of mouse DCL
SEQ ID NO 4: amino acid sequence of human DCL
SEQ ID NO 5: siDCL-2 sense RNA oligonucleotide (siRNA strand)
SEQ ID NO 6: siDCL-2 antisense RNA oligonucleotide (siRNA strand)
SEQ ID NO 7: hu-siDCL-2 sense RNA oligonucleotide (siRNA strand)
SEQ ID NO 8: hu-siDCL-2 antisense RNA oligonucleotide (siRNA strand)
SEQ ID NO 9: siDCL-3 sense RNA oligonucleotide (siRNA strand)
SEQ ID NO 10: siDCL-3 antisense RNA oligonucleotide (siRNA strand)
SEQ ID NO 11: hu-siDCL-3 sense RNA oligonucleotide (siRNA strand)
SEQ ID NO 12: hu-siDCL-3 antisense RNA oligonucleotide (siRNA strand)
SEQ ID NO 13: DCLex2C antisense RNA oligonucleotide
SEQ ID NO 14: hu-DCLex2C antisense RNA oligonucleotide
SEQ ID NO 15: DCLex2D antisense RNA oligonucleotide
SEQ ID NO 16: hu-DCLex2D antisense RNA oligonucleotide
SEQ ID NO 17: DCLex2A antisense DNA oligonuclotide
SEQ ID NO 18: hu-DCLex2A antisense DNA oligonuclotide
SEQ ID NO 19: DCLex2B antisense DNA oligonuclotide
SEQ ID NO 20: hu-DCLex2B antisense DNA oligonuclotide

FIGURE LEGENDS

Figure 1:
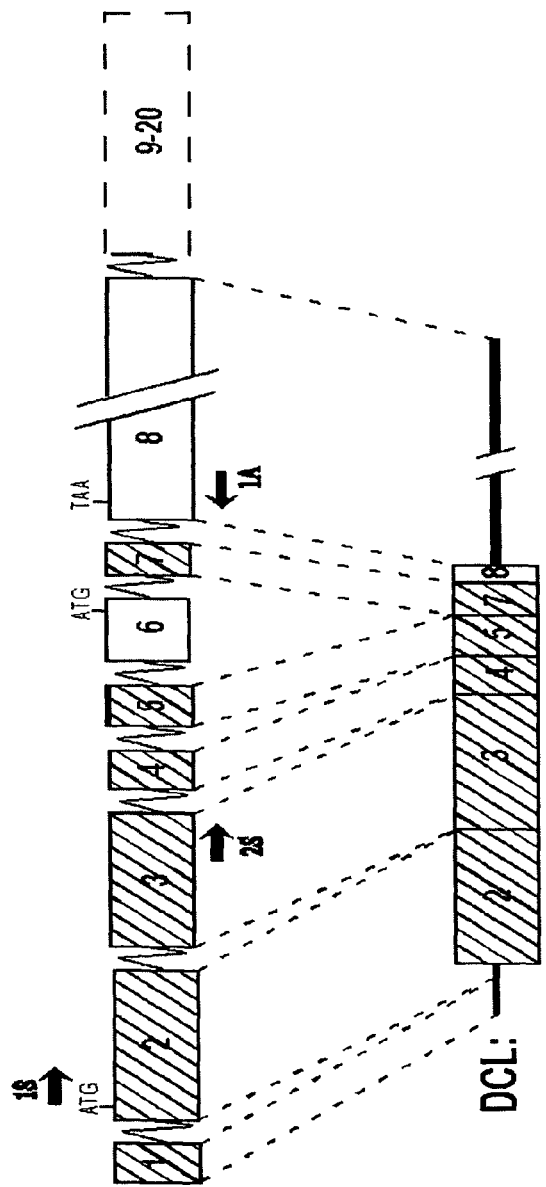

FIG. 1.—Genomic Organization of DCL and Alignment with DCX (A): Genomic organization of the DCLK gene and the cloning strategy of the DCL cDNA. Only the exon-intron structure of the DCL part is indicated including the recently identified exon 8 encoding the common 3' end of CARP and DCL (Vreugdenhil et al., 2001, supra). Exons are represented by rectangles and indicated by arabic numbers; introns are solid lines. The DCL transcript is indicated below (DCL) the genomic structure. The ORF is represented by a rectangle, non-translated sequences by lines. The location of the primers, used to clone DCL, is indicated by arrows.

(B): Alignment of the DCL (SEQ ID NO: 3) protein with DCX (SEQ ID NO: 28). Identical residues are dark grey and conserved substitutions are light grey. The two DCX domains and the SP-rich domain FIG. 2.—DCL is a M.A.P. and Stabilizes Microtubules Panel I:

(A-C) DCL overexpression in COS-1 cells.

(D-F) DCL overexpressed in COS-1 cells treated with colchicine.

Green represents DCL; red represents α-tubulin and yellow indicates DCL colocalization with α-tubulin. Blue represent DNA (nucleus). Arrows indicate DCL associated microtubule bundles, which are resistant to coichicine treatment. Also note the clear association with a centrosome in A and B. Scale bar is 10 μm.

Panel II. Microtubules polymerization in vitro by DCL. Different concentrations of recombinant DCL protein were incubated with purified tubulin and the turbidity of the DCL/tubulin mixture was monitored at 340 nm for 30 min. Taxol was used as a positive control and water as a negative control. The graph shown is a typical example from multiple experiments (N=4) with similar results.

FIG. 3.—Expression of DCL is Developmentally Regulated (A): Cross-reactivity of DCX and DCLK recognizing antibodies. Western blot analysis of lysates of COS-1 cells overexpressing DCL (lane 4-6) or two different DCX variants (lane 2 and 3) with anti-DCX (upper panel) or anti-DCLK (lower panel). Anti-DCLK strongly recognizes DCL (lane 4-6).

(B): Onset of DCL and DCX protein during embryogenesis. Immunoblots of embryonic brain fractions from age ED8 to ED18 and adult were stained with anti-DCLK and anti-DCX. As a positive control for the CARP/DCL antibody, an extract of COS-1 cells overexpressing DCL was used.

(C): Western blot analysis of DCL and DCX in various adult brain regions. 1: ED12 head (positive control), M: Molecular weight marker 2: cerebellum, 3: brain stem, 4: hypothalamus, 5: cerebral cortex, 6: hippocampus 7: olfactory bulb.

Figure 4:
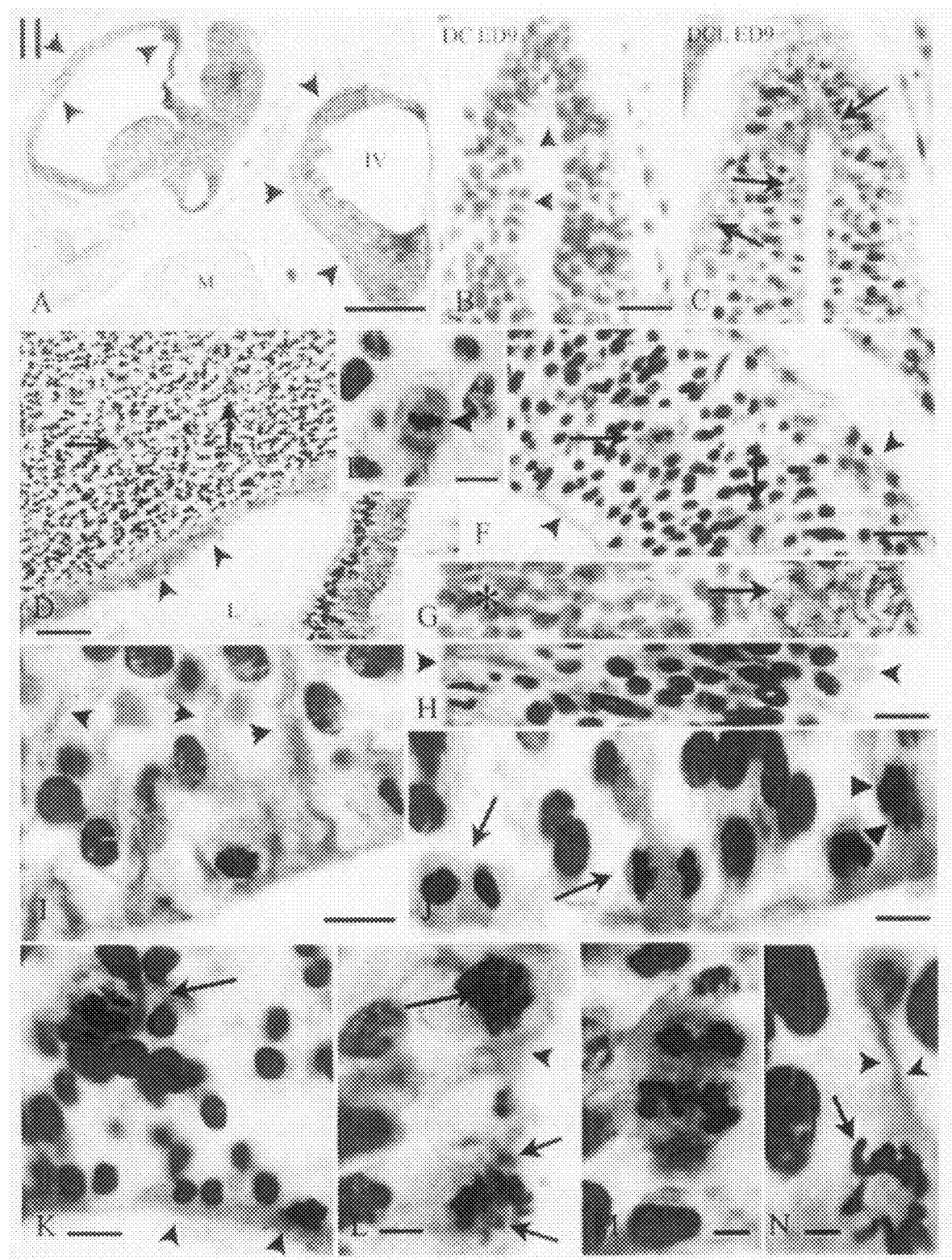

FIG. 4.—Localization and Ontogeny of DCL Expression in Embryonic Brain

I.: In situ hybridization of a transversal brain section of embryonic day (ED) 8 (panel A); and sagittal sections at ED10 and ED12 (panel B and C, respectively). On ED8 and ED10, the signal was low but increased considerably at ED12. Abbreviations: di—diencephalon, lv—lateral ventricle, me—mesencephalon; mo—medulla oblongata, mt—metencephalon, mv—mesenchephalic vesicle, nc—neopallial cortex, ne—neuroepithelium, rh—rhombencephalon, te—telencephalon, tv—telencephalic vesicle, IV v—4th ventricle. Scale bar: 1 mm; exposure time: 14 days).

II: DCL protein distribution in the early mouse neuroepithelium.

A: DCL protein distribution at ED11 (sagittal section). Staining is restricted to the proliferative regions (telencephalon and diencephalon on the left and right, respectively) and found in the outer layers close to the pia as well as in the inner ventricular zone (arrowheads; see also higher magnifications below), whereas normeuronal tissue like the mandibular component of the first branchial arch (M) is devoid of any signal. IV; fourth ventricle. Bar represents 150 μm.

B+C: Adjacent transversal (coronal) sections from the early neuroepithelium at ED 9 immunostained for DCX (B) and DCL (C). No DCX staining is observed (arrowheads in B), whereas DCL is already expressed both in the inner ependymal (upper 2 arrows) as well as in outer, marginal region (lower arrow). Bar represents 25 μm.

D: Sagittal section of the neuroepithelium of the neural tube at ED11, showing abundant expression at the luminal border (arrowheads), while in the developing neuronal tissue, isolated dividing cells are immunopositive as well (arrows). L indicates the neural lumen of the neural tube. Bar represents 70 μm.

E: Detail of a DCL-immunopositive mitotic cell in the neuroepithelium. The chromosomes (arrowhead) oriented in the midline cleavage plane are obvious. Bar represents 3 μm.

F: Overview of the neuroepithelium of the telencephalon at ED10, showing DCL expression in the ventricular (ependymal) layer (arrowhead on the left) as well as on the marginal/cortical plate zone (arrowhead on the right). 2 immunopositive doublets of dividing cells in the intermediate zone are also visible (arrows). Bar represents 15 μm.

G+H: Transversal cross-sections of the cortical neuroepithelium, illustrating the differential, yet partly overlapping, distributions of DCX and DCL. DCX is not expressed until ED11 (G), and mainly in the uppermost part of the cortical plate and marginal/cortical plate region (arrow) of the cortical neuroepithelium. DCL, in contrast, is already expressed at ED9 (H) at particularly high levels in the ventricular (ependymal) layer (arrowhead to the left) with lower levels in the intermediate and marginal zones (arrowhead to the right). Note that the ventricular layer (asteriks in G) is devoid of DCX signal. Bar represents 5 μm.

I: Detail of the ependymal layer of the ventricular zone at ED9 showing DCL Expression in fibers extending from the neuroepithelium into the intermediate zone (arrowheads). Bar represents 12 μm.

J: Detail of the ependymal layer showing clear immunoreactivity in dividing neuroepithelial cells adjacent to the lumen, that are in; telophase (left), anaphase (middle), while also a DCL positive cell in mid prophase is visible that appears to divide vertically (arrowheads) while migrating away from the lumen (right). Bar represents 8 μm.

K: DCL immunoreactivity in the ependymal layer at ED11, in cells in prophase and telophase (arrowheads) as well as in a blast-like cell in metaphase/anaphase (arrow). Bar represents 10 μm.

L: Two DCL immunopositive mitotic cells in the ependymal layer displaying intense immunoreactivity also in the centrosome-like structures (lower arrows). Bar represents 1.5 μm.

M+N: Examples of 2 DCL immunopositive, dividing cells in anaphase II/telophase II (M) and in metaphase/anaphase I, with the chromosomes clearly visible (arrow), while also some microtubular staining is observed (arrowheads). Bars represent 1 μm.

FIG. 5.—DCL expression in Neuroblastoma cells.

Panel I:

A: DCL is endogenously expressed in several neuroblastoma cell-lines. Screening by Western Blot analysis for DCL positive cell lines. Lane 1: COS-1 cells, lane 2: Hela cells, lane 3: NG108-15 cells, lane 4: NS20Y cells, lane 5: N1E-115 cells, lane 6: molecular weight marker, lane 7: SHSY5 cells. Note that DCL is expressed in neuroblastoma cell lines (lane 3, 4, 5 and 7) but not in cell lines from non-neuronal origin (lane 1 and 2).

B: DCL is a phosphoprotein. NG108-15 lysates stained with anti-DCL. Lane 1: untreated lysate, lane 2: lysate incubated at 37° C. without phosphatase, lane 3: lysate incubated at 37° C. with phosphatase. Lane 4-6 are similar as 1-3 but with DCL overexpression. Note that endogenous DCL comigrates with overexpressed DCL in lane 4-6.

Panel II:

Western blot analysis of DCL expression in N1E-115 cells with (1 to 3) and without (4) siRNA treatment performed in duplo. Three different siRNA molecules targeting DCL were used: siDCL-1 (lanes 1), siDCL-2 (lanes 2) and siDCL-3 (lanes 3). Note that siDCL-2 and 3 lead to an effective knockdown while siDCL-1 failed to do so. As a reference, the same membrane was re-stained with α-tubulin.

Panel III.

Knock-down of DCL leads to relaxation of the microtubule cytoskeleton in interphase. Anti-DCLK (green) staining yields a spickled pattern, which is most prominent near the nucleus (A) in non-treated cells (A-C). This pattern is not affected by siDCL-1 (D) but anti-DCLK staining is almost absent by effective DCL knockdown by siDCL-3 (G). The cytoskeleton, as indicated by α-tubulin staining (B, E and H), has a fine-maze structure in non-treated cells (B) and in cells treated with si-DCL-1 (E) but is greatly relaxed by siDCL-3. Merged illustrations of DCL and α-tubulin staining show non-treated cells (C), cells transfected with siDCL-1 (F) and cells transfected with siDCL-3 (I). Green=DCL, Red=α-tubulin, Yellow=colocalization of DCL and α-tubulin. Scale bar is 10 μm.

Panel IV:

DCL knock-down does not affect centrosome structure. Spickled anti-DCLK staining (A, D, G) is highly concentrated (A, D) around centrosomes as indicated by anti-γ-tubulin staining (B, E and H) and effective knock-down of DCL (G) does not lead to obvious changes in the structure or form of centrosomes (I). Merged illustrations of DCL and α-tubulin staining are shown of non-treated cells (C), cells transfected with siDCL-1 (F) and cells transfected with siDCL-3 (I). Green=DCL, Red=γ-tubulin, Yellow=colocalization of DCL and γ-tubulin. Scale bar is 10 μm.

Figure 6:
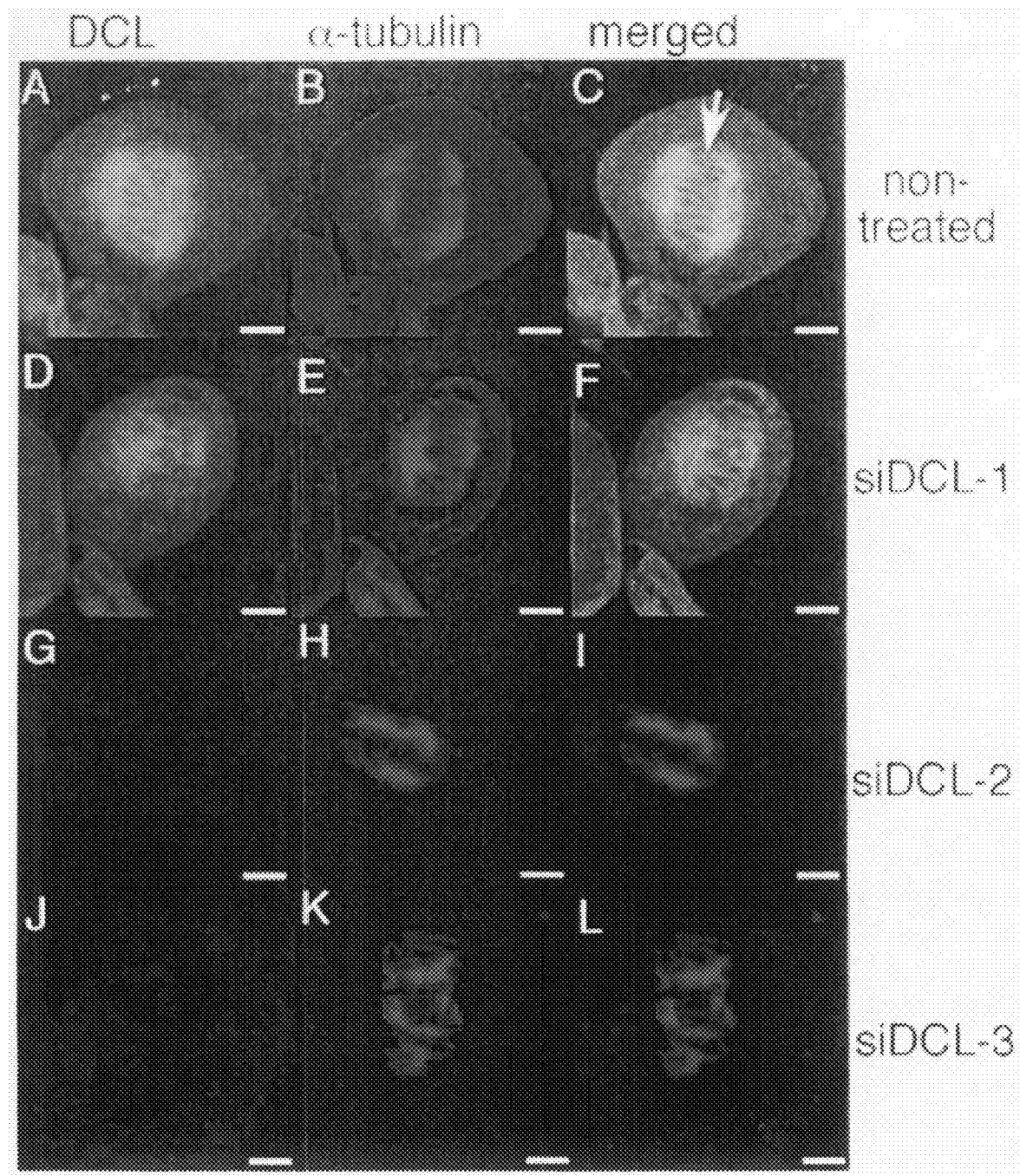

FIG. 6.—DCL knock-down leads to deformation of mitotic spindles. In non-treated cells (A-C) DCL (A) largely colocalizes with α-tubulin (B). The merged image (C) indicates DCL presence at the kinetochore (arrow). Transfection with siDCL-1 (D-F) did not lead to a DCL knockdown (D) and also did not change the formation of mitotic spindles as indicated by α-tubulin staining (E). Effective DCL knockdown by siDCL-2 (G-I) or siDCL-3 (J-L) lead to a disappearance of DCL (G, J) and to the disappearance (H) and deformation (K) of mitotic spindles as indicated by α-tubulin staining. Green=DCL, Red=α-tubulin, Yellow=colocalization of DCL and α-tubulin. Scale bar is 10 μm.

Figure 7:
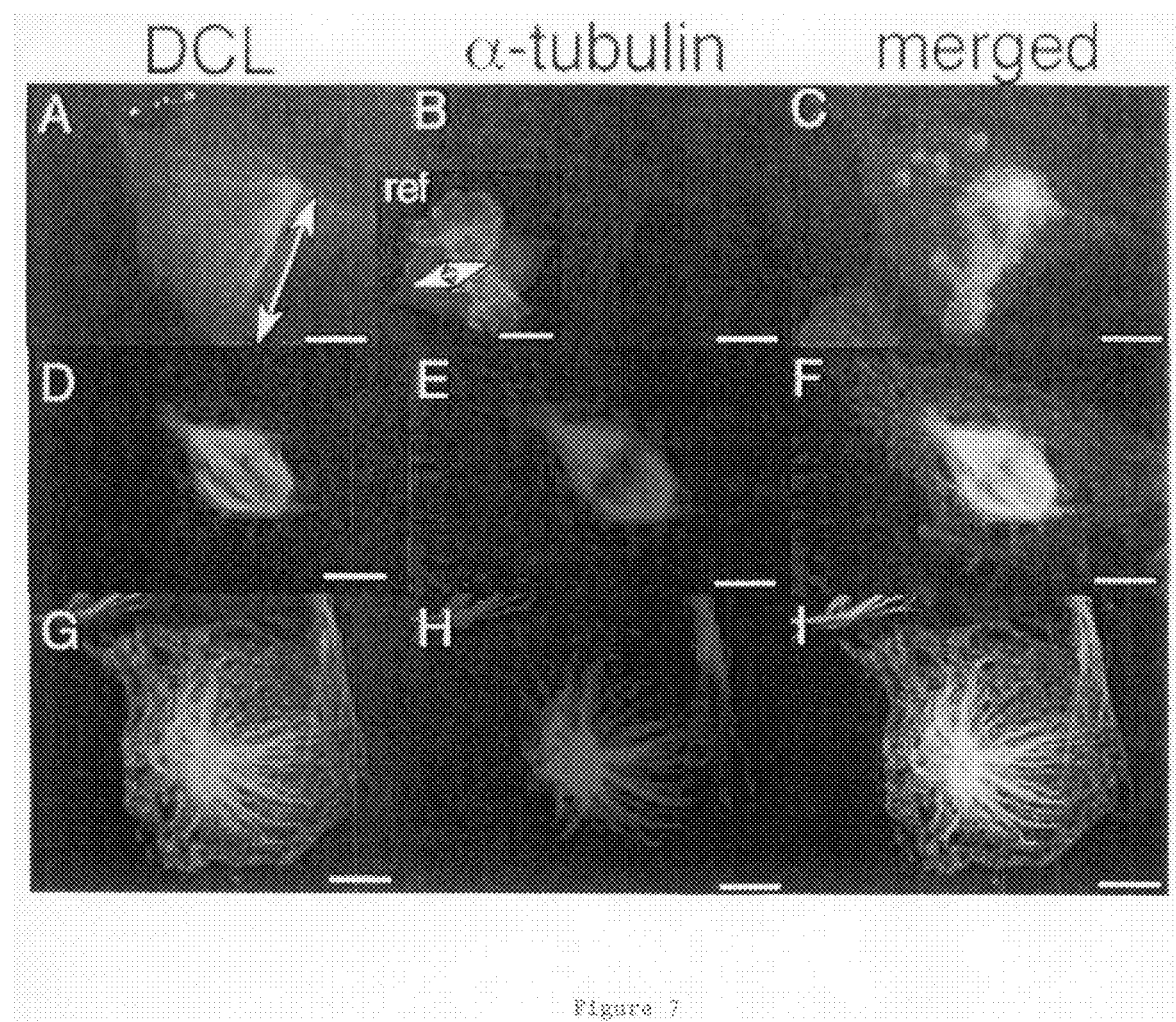

FIG. 7-DCL overexpression in dividing COS-1 cells.

A-C: Immunocytochemical analysis of DCL overexpression. A normal dividing COS-1 cell stained with α-tubulin is shown as reference (ref). Overexpression of DCL (Green, A) leads to elongation of mitotic spindles as indicated by co-staining with α-tubulin (B). Note the difference in mitotic spindle length, indicated by arrows, of transfected versus nontransfected cells. DNA is stained with DAPI (blue).

D-I: Confocal microscopy of DCL overexpression in COS-1 cells during cell division. One phenotype looks similar (D-F) to wildtype COS-1 cells in which DCL (D) largely colocalizes with α-tubulin (E). Similar to endogenous localization of DCL in dividing N1E-115 cells, DCL also is located at the kinetochore. DCL localization is shown in green, which overlaps with mitotic spindles as indicated by α-tubulin staining (red). The other phenotype observed lead to elongation and altered orientation of the mitotic spindles (G-I). Green=DCL (A, D, G), Red=α-tubulin (B,E,H), Yellow=colocalization of DCL and α-tubulin (C, F, I). Scale bar is 10 µm.

The file of this patent contains at least one drawing executed in color. Copies of this patent with color drawings will be provided by the Patent and Trademark Office upon request and payment of the necessary fee

EXAMPLES
Example 1

Cloning of DCL from Mouse and Human

DNA sequence analysis of a DCL cDNA clone from mouse (SEQ ID NO: 1) revealed an open reading frame of 362 amino acids (SEQ ID NO: 3) with a predicted molecular mass of 40 kDa (FIG. 1B) and 73% amino acid identity (81% similarity) with mouse DCX over the entire length of both proteins. Alignment of the two predicted DCX repeats (Taylor et al., 2000, supra) with mouse DCX revealed an even higher amino acid identity of 81% (89% similarity) for DCX domain 1 and 90% amino acid identity (99% similarity) for DCX domain II, strongly suggesting that this latter domain has a similar function in both proteins. The serine/proline (SP)-rich C-terminus, which corresponds largely with CARP (Vreugdenhil et al., 1999, Neurobiology 39, 41-50), exhibits a lower amino acid identity of 63% (78% similarity). This SP-rich domain is present in both DCX and DCL. Such SP-rich domains are potential MAP kinase motifs (Sturgill et al., 1988, Nature 334, 715-718), suggesting that the C-terminus is a MAP kinase substrate. Interestingly, the YLPL motif in this region of DCX has been shown to interact with AP-1 and AP-2 and has been implicated in protein sorting and vesicle trafficking (Friocourt et al., 2001, Mol. Cell Neurosc. 18, 307-319). In DCL, however, the corresponding motif is YRPL in which a hydrophobic leucine is replaced by a basic arginine residue, indicating that DCL is not likely to interact with AP-1 and AP-2.

The human dcl cDNA/mRNA (SEQ ID NO: 2) and protein (SEQ ID NO: 4) sequences were obtained from a human neuroblastoma cell line (SHSY5) using the mouse sequences and were found to be very similar to the murine sequences, as described elsewhere herein.

Example 2

DCL is a MAP (Microtubule Associated Protein) and Stabilizes the Cytoskeleton The two DCX domains of both DCX and DCLK-long have been shown to interact with and to stabilize microtubule structures (Francis et al., 1999, supra; Gleeson et al., 1999 supra; Kim et al., 2003, Struct. Biol. 10, 324-333; Lin et al., 2000, supra). As DCL contains DCX domains that are identical to DCLK-long, a similar stabilizing and polymerizing effect on microtubules was expected for DCL. To confirm this, three types of experiments were conducted: first, overexpression of DCL in COS-1 cells resulted in a fibrillar staining pattern in the soma overlapping the microtubule distribution (FIG. 2.I A), as shown by co-localization with α-tubulin antibodies (FIGS. 2.I B and C). Second, to test if DCL-containing microtubule bundles exhibit a similar resistance to depolymerization as is known for DCX and other MAPs, DCL transfected cells were exposed to 10 µg colchicine, a compound which depolymerizes and disrupts tubulin microtubules. Non-transfected cells exhibited clear depolymerization of the microtubule cytoskeleton, whereas the microtubule cytoskeleton of all DCL transfected cells was resistant to 1 hr colchicine treatment, in particular in condensed microtubule/DCL bundles (FIG. 2.I D-F). This showed that DCL, similar to DCLK-long and DCX, is capable of stabilizing microtubules. Third, in an in vitro polymerization assay the microtubule polymerizing properties of DCL were tested by incubating different concentrations of recombinant, non-tagged DCL with purified tubulin. Taxol was used as a positive control, which is a well-known microtubule polymerizing compound. Spectrophotometrical monitoring of microtubule polymerization revealed that DCL polymerizes microtubules in a dose-dependent manner (FIG. 2.II). Together, these data showed that DCL, like DCLK-long and DCX, can directly polymerize and stabilize microtubules.

Example 3

Characterization of a DCL Recognizing Antibody

Recently the generation of an antibody against CARP, called anti-CaMKLK, has been described (Kruidering et al., 2001, supra) which also recognizes other splice-variants of the DCLK gene including DCLK-short (also known as cpg16 (Silverman et al., 1999, J. Biol. Chem. 274, 2631-2636) or CaMLK). CARP is a small protein of 55 amino acids of which 43 are identical with the C-terminus of DCL, that shares 70% amino acid homology with human DCX (Vreugdenhil et al., 1999). To address the specificity of anti-CaMLK, DCX and DCL were overexpressed in COS-1 cells and analysed for possible cross-reactivity by Western Blot analysis. Anti-CaMLK strongly recognized DCL (FIG. 3A lane 4-6) whereas only some cross-reactivity was observed with DCX (FIG. 3A lane 2 and 3). On the other hand, the DCX antibody used herein, raised against the C-terminal 17 amino acid of DCX, strongly recognized DCX (FIG. 3A lane 2 and 3) and not DCL (FIG. 3A lane 4-6). Thus, anti-CaMLK strongly recognizes numerous splice variants of the DCLK gene including DCLK-short and DCL and therefore is herein referred to as "anti-DCLK". In addition, some cross-reactivity of anti-DCLK with DCX may occur, whereas the DCX antibody is specific for DCX alone and not for DCL.

Example 4

DCL is Highly Expressed at Early Stages of Brain Development

Western blot analysis of embryonic brain homogenates revealed the presence of a 40 kDa protein immunopositive for anti-DCLK. The size of this protein corresponds with that of the recombinant DCL protein overexpressed in COS-1 cells (FIG. 3B). Anti-DCLK recognizes only DCL in the developing mouse brain as no other immuno-reactive bands were observed (FIG. 3B lane 8-18). Although signal was already present at ED10, highest levels of immunoreactive DCL protein were found at ED12 and ED14. The level of DCL protein declined after ED14 and a weaker but clear 40 kDa band was still present in adult brain. Here, an additional band of 53 kDa was very prominent (FIG. 3B). In agreement with its molecular weight of 53 kDa, this band most likely represented DCLK-short, which is abundantly expressed only in adult and not developing brain (Vreugdenhil et al, 2001; Omori et al., 1998). Within the adult brain, highest levels of DCL protein were found in the olfactory bulb, with lower levels in the hippocampus and cerebral cortex, and very low levels in cerebellum, brain stem and hypothalamus (FIG. 3C).

DCX has been reported to be specifically expressed during development but to drop below detection level in adult brain (Francis et al., 1999 supra; Gleeson et al., 1999 supra), although DCX remains expressed in very low amounts in selected regions (Nacher et al., 2001, Eur J Neurosci 14, 629-644). For comparison to the DCL findings, the protein lysates were further analysed with a DCX-specific antibody recognizing the C-terminus. In agreement with other studies (Francis et al., 1999; Gleeson et al., 1999), the highest concentrations of DCX were found at ED12 and were found to decline afterwards (FIG. 3B).

In contrast to DCL, no DCX protein expression, also after prolonged exposure, could be detected in embryo heads of ED8 and ED10 or in the adult brain. However, consistent with a role for DCX in neuronal migration, DCX immunoreactivity was observed in the adult olfactory bulb (FIG. 3C lane 7), but not in other brain structures (FIG. 3C lane 2-6), indicating dilution of DCX below detection level in the whole brain lysates.

To analyze regional differences in DCX and DCL expression in more detail, the spatio-temporal expression of DCL during early embryonic development was studied using in situ hybridization. Low levels of DCL mRNA expression were observed along the length of the neuroepithelium (destined to give rise to the central nervous system and the layered cortex in later stages of development) at ED8 (FIG. 4.I A). At ED10, when massive divisions start to become prominent, substantial expression was found in the early diencephalon, telencephalon and mesencephalon, a.o. (FIG. 4.I B). Consistent with the RT-PCR and Western blot experiments the intensity of DCL expression at ED12 increased profoundly (FIG. 4.I C) as compared to ED 8 and 10, with high levels in the proliferative ventricular zones.

To study the spatio-temporal distribution of DCL protein, immunohistochemistry was performed on sections from mouse embryos at 8, 9, 10, and 11 days old using the DCLK antibody (anti-DCLK) that recognizes DCL exclusively at these ages (see above and FIG. 3B). At ED8, no DCL staining was observed (data not shown). However, at ED 9, an age at which no DCX protein expression is found yet (FIG. 4.II B), DCL signal was prominent in the ventricular walls and main neuroepithelia, well-defined areas of massive mitosis and neurogenesis (FIG. 4.II C and J). At ED10 and 11, DCL protein generally followed the in situ hybridization pattern, with high levels in the proliferative regions of the central and peripheral nervous system, including the telencephalon, diencephalon, lateral ganglionic eminence, the neuroepithelium of the neural tube, as well as e.g. the dorsal root and sympathetic ganglia, whereas non-neuronal tissues like bone or the intestines e.g., were devoid of any signal (FIG. 4.II A and D). Higher magnifications of the early neocortex, revealed DCL expression not only in the upper layers of the cortical plate, but also in the inner ventricular zone, with lower levels apparent in the intermediate zone (FIG. 4.II F and H).

A particularly striking observation was the DCL immunoreactivity in mitotic cells, in e.g. the ventricular zone and epithelial wall (examples in FIG. 4.II C-F, H, J-N), while also DCL positive, mitotic cells were found in the neuroepithelium of the neural tube (FIG. 4.II D) and the intermediate zone of the cortical neuroepithelium (FIG. 4.II F), generally with a more isolated occurrence and at lower frequencies. In addition to the DCL staining pattern of the epithelia in the same section, clear immunopositive doublets were observed (FIG. 4.II D and F). Also mitotic cells in specific stages of the cell cycle could be recognized (FIG. 4.II J-N), with intense immunoreactivity between chromosomes and even immunopositive centrosome-like structures (FIG. 4.II L) clearly visible.

Taken together, the data clearly showed that presence of DCL mRNA expression precedes that of DCX starting already from ED8, and DCL protein from ED9 onwards. Highest expression of DCL mRNA and protein was found at ED12 and ED14, respectively, while, contrary to DCX, also transcript and protein expression of DCL was found on Western blots from adult brain. Protein distribution during early development is not only different from that of DCX in time, but also in location, i.e., DCL was found in the ventricular zone and cortical plate rather than the cortical plate alone (FIG. 4.II C, F-H). Most strikingly, DCL immunoreactivity was regularly found in mitotic cells of the neuroepithelium and sometimes in the intermediate zone.

Example 5

DCL is Endogenously Expressed in Neuroblastoma Cells

To investigate a possible role for DCL in neuronal proliferation, the endogenous DCL expression in several neuronal cell lines was analysed. A DCL immunoreactive band of approximately 40 kDa was observed in 4 different neuroblastoma cell lines, that was absent in any of the non-neuroblastoma cell lines studied (FIG. 5.I A), indicating specificity for DCL expression in cells with a neuroblast-like phenotype. Screening of other non-neuroblastoma cell lines including PC12 cells, failed to identify any DCL positive cell-line (data not shown). In the neuroblastoma cell line N1E-115, the 40 kDa immunoreactive doublet co-migrated with the doublet resulting from overexpressing DCL (FIG. 5.I B). This 40 kDa band could not be explained by the presence of DCX in N115 cells since both RT-PCR experiments and Western blot analysis failed to detect DCX signals using DCX-specific primers and antibodies (data not shown). The upper band of the 40 kDa DCL doublet therefore most likely represents a phospho-isoform of DCL, a notion that was confirmed by the disappearance of the upper band of both the endogenous as well as overexpressed DCL when the cell lysates were incubated with phosphatase. This further demonstrates that DCL, similar to DCX, is a phosphoprotein, at least in neuronal cell lines.

Example 6

DCL Affects Microtubule Architecture and Organization in N1E-115 Cells

To study function and subcellular localization of DCL, immunocytochemical experiments using confocal microscopy following manipulation of DCL expression using small interference (si) RNA technology in N1E-115 neuroblastoma cells in interphase was performed. To establish siRNA take up by N115 cells, anti-DCL synthetic siRNA molecules were labelled with Cy-5 and their presence or absence was monitored in N115 cells by fluorescent microscopy. These studies indicated the presence of anti-DCL siRNA in approximately 95% of all N115 cells (data not shown). Three different siRNA molecules against DCL were constructed: siDCL-1, 2 and 3. Western blot analysis indicated that siDCL-1 failed to knock-down DCL protein (FIG. 5.II lane 1), a finding that might be explained by the lack of TT di-nucleotides at the 3'-end in this antisense strand. siDCL-1 was subsequently used as a negative control for the effects of the siRNA procedure. Compared with non-treated cells and siDCL-1, transfection of siDCL-2 and si-DCL-3 molecules lead to a knockdown of respectively 80% and 90% as determined from Western blot analysis (FIG. 5.II lane 2 and 3). Subsequent immunocytochemical analysis of siRNA treated N115 cells using anti-DCLK and α-tubulin or γ-tubulin antibodies revealed profound effects on the architecture of the microtubule cytoskeleton of cells in interphase. In non-treated cells, anti-DCL staining was typically punctate and present throughout the remainder of the soma (see FIG. 5.III A). In contrast to DCX, which appears selectively located in the periphery of the soma and even at the extremities of neuronal processes (Friocourt et al., 2003; Schaar et al., 2004), DCL immunoreactivity was less intense at the periphery of the cell soma (FIG. 5.III A and C), and often displayed increased intensity near one, or two sides of the nucleus (FIG. 5.III A, C, D and F), suggesting that DCL is concentrated particularly along the cytoskeleton surrounding the centrosome. This subcellular location was confirmed by co-staining with the centrosome marker γ-tubulin (see FIG. 5.IV A-C).

In agreement with the Western blot analysis, transfection of siDCL-1 did not alter the endogenous DCL immunocytochemical staining pattern. DCL knock-down induced by siDCL-3, however, induced a nearly complete disappearance of the anti-DCLK staining (see FIG. 5.III G), strongly indicating that the anti-DCLK antibody recognizes DCL in N115 cells in a highly specific manner. Strikingly, in 40% of the cells transfected with siDCL-2 and in 80% of cells transfected with siDCL-3, the cytoskeleton was disrupted, as was apparent from the altered, more dispersed α-tubulin staining pattern and irregular organization. N115 cells transfected with siDCL-2 and 3 but with a normal cytoskeleton, also showed more anti-DCLK staining than cells with an aberrant cytoskeleton. This further supports a causal relation between effective DCL knock-down and subsequent abnormalities in microtubule stability. Compared to the normal microtubule cytoskeleton in non-treated cells, the abnormal pattern after DCL knockdown is characterized by bundles of microtubules with a more condensed and less dispersed structure, clearly exhibiting less side-branches (FIG. 5.III H and I). This indicated a role for DCL in branching and stabilization of the microtubule cytoskeleton.

Since DCL protein distribution was found in higher concentrations around the centrosomes, DCL knockdown may affect centrosome protein complex and subsequently nuclear positioning, cytoskeletal connectivity and (re-)organization. To address this issue, DCL knockdown was performed in combination with γ-tubulin staining (see FIG. 5.IV D-I). In agreement with the euploid nature of N115 cells, multiple centrosomes per cell were observed. However, despite efficient knock-down of DCL, no apparent change was seen in the number or structure of centrosomes, indicating that DCL is not a key factor in the structural organization of centrosomes.

Example 7

DCL is Essential for Mitotic Spindle Formation in Neuroblastoma Cells

The presence of DCL in the ventricular zone (FIG. 4) is consistent with a role for DCL in neuronal proliferation and progenitor division. Dividing N1E-115 cells were therefore analysed using confocal microscopy following DCL knockdown by siRNA. Strong DCL immunoreactivity was observed in all dividing N1E-115 cells during metaphase or early anaphase (see FIGS. 6A and D). DCL immunoreactivity largely colocalized with α-tubulin indicating an association with the mitotic spindles. However, an immunoreactive gradient was apparent for DCL in all cells analyzed, with low levels near the centrosome and high levels in the mitotic spindles and near the kinetochore, suggesting a role for DCL in the formation of mitotic spindles. Consistent with this are the dramatic effects of DCL knockdown by siDCL-2 and siDCL-3, which are associated with a complete deformation and sometimes absence of the mitotic spindles (FIG. 6 G-L). This effect on the mitotic spindles was observed in 40% of all dividing cells (siDCL-2) and in all dividing cells transfected with siDCL-3. Inefficient knockdown by siDCL-1 leaves DCL co-localization with mitotic spindles unaltered while the phenotypic appearance of mitotic spindles is similar to that of the non-treated ones mitotic spindles (FIG. 6 D-F). Thus, apparently, DCL is required for the correct formation of the mitotic spindle of dividing neuroblasts or neural progenitors.

Example 8

DCL Overexpression Leads to Elongation of Mitotic Spindles

Gain-of-function was studied by overexpressing DCL in COS-1 cells that normally do not express this protein. Consistent with the above findings on endogenous DCL expression in dividing N115 cells, DCL immunoreactivity co-localized with mitotic spindles in dividing COS-1 cells (see FIG. 7). Two different phenotypes were observed: Firstly, in 20% (n=126) of the analyzed dividing COS-1 cells, overexpression of DCL colocalized with α-tubulin, similar to the endogenous DCL expression pattern in dividing N1E-115 cells (FIG. 7 D-F), with DCL localized at the kinetochore and in mitotic spindles. However, unlike N1E-115 cells, DCL is also found associated with the centrosomes and astral fibers. Secondly, in the majority of the dividing COS-1 cells (80%), comparison of the precise mitotic stage of DCL expressing and vector-transfected cells was hampered by the fact that all DCL expressing and dividing cells showed an abnormal phenotype with elongated mitotic spindles.

Most strikingly, half-spindles were observed indicating that DCL overexpression affects centrosome segregation and spindle orientation (FIG. 7 A-C, G-I). In addition, the mitotic spindles appeared to be much longer and often thicker than the spindles from control cells (compare e.g. the spindle length of a non-transfected cell, FIG. 7B ref inset, with FIG. 7C). Notably, these DCL effects were associated with an abnormal DNA staining and distribution pattern, where the chromosomes are completely displaced and dispersed over the soma, a strikingly different pattern from the normal orientation (FIG. 7B ref inset), that is perpendicular with respect to the bipolar centrosome position (see reference length compared to FIG. 7C). Thus, overexpression of DCL in COS-1 cells leads to spindle elongation and the formation of half-spindles, suggesting that DCL plays a crucial role in mitotic spindle form and length.

Example 9

Material and Methods 9.1 Cloning of the Murine DCL

The present inventors developed an antisense primer 1A: CTGGA ATTCT TACAC TGAGT CTCCT GAG (SEQ ID NO: 21) (EcoR1 site underlined) corresponding to the stop-codon region of the CARP-specific exon and a sense primer 2S: GCAGG TTCTC ACTGA CATTA CCG (SEQ ID NO: 22) corresponding to exon 3 of the murine DCLK gene. In 30 cycles of PCR, a 457 by fragment was amplified using mouse embryonic cDNA as a template and polymerase PfuI (Stratagene). DNA sequence analysis confirmed the DNA sequence as being DCLK specific. Subsequently, a DCL cDNA encoding the complete DCL protein was amplified using CCAGGATCCACCATGTCGTTCGGCA-GAGATATG (SEQ ID NO: 23) (Bamh1 site underlined) as a sense and 1A as an antisense primer, cut with Bamh1 and EcoR1 and subcloned in the expression plasmid pcDNA 3.1 (InVitrogen, Groningen, The Netherlands). A DCL-EGFP construct was generated by subcloning a KpnI/EcoRV DCL fragment from pcDNA3.1.DCL in the SmaI/KpnI site of pEGFP-C1 (Clontech; see also FIG. 1).

9.2 In situ hybridization

DCL mRNA includes exon 8 (FIG. 1), which is absent in most other DCLK transcripts except for CARP. As CARP is expressed at very low levels during embryonic development, a 40-mer antisense oligonucleotide was developed (5' - TTTGC TGTTA GATGC TTGCT TAGGA AATGG GAAAC CTTGA-3') (SEQ ID NO: 24) complementary to an exon 8 specific sequence. As a negative control the oligonucleotide 5'- TTTGATGTTA TATGC TTGAT TAGGA CATGG GACAC CTGGA-3' (SEQ ID NO: 25) which contains 6 mismatches (underlined), was used. Both oligonucleotides were end-labelled with $\alpha$-$^{33}$P dATP (NEN Life Science Products, Hoofddorp, The Netherlands, 2000Ci/mmol, 10 mCi/ml) using terminal transferase according to the manufacturers instructions (Roche Molecular Biochemicals, Almere, The Netherlands). In situ hybridization and visualization of the signals was performed as described before (Meijer et al., 2000, Endocrinology 141, 2192-2199).

9.3 Antibodies

The generation of anti-DCL-antibodies has been described previously (Kruidering et al., 2001, supra). Mouse monoclonal anti-$\alpha$-tubulin was obtained from Sigma. Goat polyclonal anti-doublecortin (C-18) antibody, rhodamine-conjugated secondary antibodies and horseradish peroxidase-conjugated secondary antibodies were from Santa Cruz Biotechnology, Inc.

9.4 Cell Culture and Treatments

All cell culture chemicals were obtained from Life Science Technologies, Inc. unless otherwise stated. All cells were maintained at 37° C., 5% $CO_2$. COS-1 cells were cultured in Dulbecco's modified Eagles medium (DMEM), supplemented with 100 units/ml penicillin, 100 µg/ml streptomycin, and 10% Fetal Bovine Serum. NG108-15 and N115 cells were cultured in DMEM without sodium pyruvate, supplemented with 100 units/ml penicillin, 100 µg/ml streptomycin, hybridoma (HAT) mix, and 10% Fetal Bovine Serum. For transient transfection experiments, cells were cultured on plates or coverslips coated with poly-L-lysine. Primary dissociated neurons from new born mice were cultured in F-12 Ham, Kaighn's modification (Sigma) medium supplemented with L-glutamine, 100 units/ml penicillin, 100 µg/ml streptomycin, and 10% Fetal Bovine Serum. Primary neurons were isolated from the region of the hippocampus of a one day old mouse, that was incubated in a trypsin solution for 25 minutes at 37° C. Subsequently, the cells were washed twice with culture medium and plated on coverslips coated with poly-L-lysine. 24 Hours later, the culture medium was replaced and supplemented with 7.5 µM cytosine-β-D-arabinoside (Sigma) to reduce the amount of glia cells. The transient transfection experiments were performed with Superfect (Qiagen, Valencia, Calif.) according to manufacturers instructions. Primary neurons were transfected four days after isolation.

9.5 siRNA Experiments

For siRNA experiments, the mouse neuroblastoma cell-line NIE-115 (ATCC number CRL-2263) was used. Synthetic RNA oligonucleotides 5'-CAAGA AGACG GCUCA CUCC-3' (SEQ ID NO: 26) and 5'-GGAGU GAGCC GUCUU CUUG-3' (SEQ ID NO: 27) (annealed siDCL-1), 5'-CAAGA AGACG GCUCA CUCCT T-3' (SEQ ID NO: 5) and 5'-GGAGU GAGCC GUCUU CUUGT T-3' (SEQ ID NO: 6) (annealed siDCL-2) and 5'-GAAAG CCAAG AAGGU UCGAT T-3' (SEQ ID NO: 9) and 5'-TCGAA CCUUC UUGGC UUUCT T-3' (SEQ ID NO: 10) (annealed siDCL-3) in which the 3' thymidines are deoxynucleotides, were obtained from Eurogentec and dissolved in annealing-buffer (100 mM KAc, 30 mM Hepes pH7.5, 2 mM MgAc) to a final concentration of 100 pM. For the siRNA duplex formation, equal molar amounts of sense and antisense oligonucleotides were mixed, heated at 94° C. for 1 minute followed by incubation at 37° C. for 1 hour. Per well a final concentration of 100 nM siRNA duplex was used. For gene silencing, 60 pmol siRNA duplex was dissolved in 50 µl opti-MEM (Life Technologies) and mixed by pipetting with 3 µp1 oligofectamine reagent (Invitrogen), dissolved in 12 µl opti-MEM. After 20 minutes incubation at room temperature, the volume was increased with 32 µl opti-MEM and the total mixture (100 µl) added to the cells (500 µl). After 48 hours, gene silencing was tested by Western blot analysis and immunofluorescence.

9.6 Immunocytochemistry

Cells were cultured and transiently transfected as described above. At the indicated times, cells on coverslips were fixed with 80% aceton in water for 5 minutes at room temperature. Cells were then rinsed twice with phosphate-buffered saline (PBS), 0.05% Tween 20 and blocked for at least 1 hour in blocking buffer: PBS, 0.05% Tween 20, 5% Normal Goat Serum (NGS, Sigma). Primary antibody was added for 1 hour at room temperature in blocking buffer, washed 3 times with PBS, 0.05% Tween 20 and incubated with rhodamine-conjugated second antibodies for 30 minutes at room temperature in blocking buffer. Following another wash, the nuclei were stained with 0.2 µg/ml Hoechst 33258 for 5 minutes, washed 4 times and analyzed. Images were obtained with an Olympus AX70 fluorescent microscope coupled to a Sony 3CCD color video camera operated by Analysis® software (Soft Imaging System, Corp.). To map DCL protein distribution, embryonic CD 1 mouse embryos of ED 9, 10 and 11 were shortly washed in PBS and then fixed for 4 h in methanol/acetone/water (40:40:20)(MAW, Franco et al, 2001) at room temperature and then stored in ethanol 70% for 2 weeks, before being embedded in Paraplast Plus (Kendall, Tyco Healthcare, Mansfield, Mass. 02048, USA) after which 6 μm thick sections were mounted on Superfrost Plus slides (Menzel-Gläser). TBS was used as a washing buffer in all following steps. After clearing in xylene and graded ethanol, sections were post-fixed in Bouin's fixative, prior to washing and blockage of endogenous peroxidase activity by 15 min 0.1% hydrogen peroxide treatment. To reduce aspecific binding, 1% milkpowder solution (Campina, The Netherlands) in PBS was applied for 30 min. The primary DCL antibody was applied 1:50 in 0.25% gelatin/0.5% triton X-100 in TBS (Supermix) for 1 hour at room temperature and then overnight at 4° C. Secondary antibody (biotinylated anti-rabbit, Amersham Life Sciences, 1:200) incubation was in Supermix for 1 h 30 min at room temperature, amplified with avidin-biotin (ABC) Elite (Vector Laboratories, Burlingame), biotinylated tyramide (1:500) with 0.01% peroxide for 30 min followed by another 45 min incubation with ABC. The last 2 washes were in 0.05 M Tris HCl buffer (pH 7.6), which was also used to dissolve diaminobenzidine (DAB) (0.05 M). Sections were counterstained with cresyl violet and coverslipped with Entellan (Merck).

For comparison, also DCX protein distribution was mapped in adjacent sections, using the C-18 Doublecortin specific antibody (Santa Cruz Biotechnology, South Cruz Calif., USA) at a 1:75 dilution. The same protocol was used as above, except for the blocking step in milkpowder solution that was omitted and an biotinylated anti-goat as secondary antibody.

9.7 Protein Extraction and Western Blotting

Mouse tissue and cells were solubilized with lysis buffer (20 mM triethanolamine pH 7.5, 140 mM NaCl, 0.05% deoxycelate, 0.05% dodecyl sodium sulfate, 0.05% Triton X100, supplemented with Complete™ EDTA-free protease inhibitor mixture (Roche Molecular Biochemicals) and centrifuged at 16,000 g for 30 minutes. Supernatant was collected and protein concentration determined using the Pierce method. Equal amounts of protein were separated by SDS-PAGE, transferred to immobilon-P PVDF membranes (Millipore). Blots were blocked for 1 hour with blocking buffer (Tris-buffered saline, 0.2% Tween 20 (TBST), 5% milk), incubated with primary antibodies in blocking buffer for 1 hour, washed 3 times with TBST, incubated with horseradish peroxidase-conjugated secondary antibodies in blocking buffer for 30 minutes and washed 3 times with TBST. Antibody binding was detected by ECL (Amersham Pharmacia Biotech).

9.8 Phosphatase Treatment

DCL transfected and untransfected N1E-115 cells were solubilized with lysis buffer (50 mM Tris-HCl pH 9.3, 1 mM $MgCl_2$, 0.1 mM $ZnCl_2$, 1 mM spermidine supplemented with Complete™ EDTA-free protease inhibitor mixture (Roche Molecular Biochemicals), centrifuged at 16,000 g for 30 minutes. Supernatant was collected and protein concentration was determined using the Pierce method. Each supernatant was divided in 3 samples containing 50 μg of protein. One sample was untreated, the second incubated for 30 minutes at 37° C. without enzyme and the third was incubated with 10 units of Calf Intestinal Alkaline Phophatase (Promega Bioscience, Inc.). The samples were analyzed by Western blotting as described above.

9.9 Tubulin Polymerization Assay

DCL encoding cDNA was excised from the pcDNA3.1 expression construct and re-ligated into pET28 using BamH1 and EcoR1. The resulting DCL expression construct was transfected into BL21 cells. A single colony was grown in 500 ml LB to OD 0.7, at which point IPTG was added to a final concentration of 0.4 mM. After three hours of induction, bacteria were collected, washed with PBS and pelleted. Recombinant DCL protein was isolated by re-suspending the pellet and passing it through a French press after which it was purified using the Probond (Invitrogen) $Ni^{2+}$ affinity resin according to the manufacturer's instructions. Purified DCL was concentrated to 0.8 mg/ml using a Centricon 30 concentration device. Tubulin polymerization assays were performed according to Gleeson et al (Gleeson et al., 1999, supra) using the tubulin polymerization assay kit (cat no BK006) from Cytoskeleton. Briefly, 1 mg tubulin was dissolved in 1.1 ml ice cold polymerization buffer according to the manufacturer's instructions and 100 μl of this was added to 10 μl DCL protein of various concentrations in a 96-wells microtiter plate. Subsequently, absorption at 340 nm was measured for 30' in 30" intervals using the HTS2000 (Biorad/Perkin Elmer).

Dcl and DCL SEQUENCES

```
SEQ ID NO: 1
ccacgcgtcc  gcggagaacc  gcatttcaat  gaggaccagc  tccagcgcat  cagtgcacta
gcggtcgcag  cttccagacg  ctcgtgctcc  gcagcccag   ccgcgcccag  cccggcgagg
acagctccag  cagccggcca  cagacaaccc  agcctccacc  cgcgaccggt  tccataagca
agccagccat  gtcgttcggc  agagatatgg  agttggagca  ttttgatgag  cgggacaagg
cgcagaggta  cagcagggg   tcccgtgtga  atggcctgcc  cagcccaca   cacagcgccc
actgcagctt  ctaccgcacc  cgcaccctgc  agacactcag  ctccgagaag  aaagccaaga
aggttcgatt  ctacagaaat  ggtgaccgct  acttcaaagg  aattgtgtat  gccatctccc
cagaccgctt  cagatctttc  gaggccctgc  tggctgattt  gacccgaact  ctctcggata
atgtgaattt  gcccagggg   gtgagaacca  tctacaccat  cgatggactc  aagaagatct
ccagcctgga  ccagctggtg  gaaggtgaaa  gctatgtctg  cggctccatc  gagcccttta
agaagctgga  gtacaccaag  aatgtgaacc  ccaactggtc  agtgaacgtc  aagaccacct
cagcctcccg  cgcagtgtct  tctttggcca  ctgccaaggg  tgggccttcg  gaggttcggg
agaataagga  tttcattcga  cccaagctgg  tcaccatcat  cagaagtggg  gtgaagccac
ggaaggctgt  cagaatcctg  ctgaacaaga  agacggctca  ctccttcgag  caggttctca
ctgacattac  cgacgctatc  aagctggact  ccggtgtggt  gaagcgcctg  tacactctgg
atgggaagca  ggtgatgtgc  cttcaggact  ttttttggtga  cgatgacatt  tttattgcat
gtggaccaga  gaagttccgt  taccaggatg  atttcttgct  agatgaaagt  gaatgtcgag
tggtgaaatc  aacttcttac  accaaaatag  catcagcgtc  ccgcagaggc  acaaccaaga
gcccaggacc  ttcccggaga  agcaagtccc  cagcctccac  cagctcagtt  aatggaaccc
```

-continued ctggtagtca gctctctact ccacgctcgg gcaagtcacc aagtccatca cccaccagcc
caggaagcct gcggaagcag agggacctgt accgccccct ctcgtcggat gatttggact
caggagactc agtgtaagaa ttc SEQ ID NO: 2
gcacatccct gcactagtgg ccgcaaccga gacgccgcgc tccagcagct gctgccgccc
agcccggccc cgccgccgcc ccccagccct gcagcccgc agcccgcc gcgcccagcc
cggcgaggac agcaccagga ggcggccccc agcgcggcca caaagacccc cggcggcgtc
tctccgcgga ccggtcctac ttgaagtcca tcatgtcctt cggcagagac atggagctgg
agcacttcga cgagcgggat aaggcgcaga gatacagccg agggtcgcgg gtgaacggcc
tgccgagccc gacgcacagc gcccactgca gcttctaccg cacccgcacg ctgcagacgc
tcagctccga gaagaaggcc aagaaagttc gtttctatcg aaacggagat cgatacttca
aagggattgt gtatgccatc tccccagacc ggttccgatc ttttgaggcc ctgctggctg
atttgacccg aactctgtcg gataacgtga atttgccca gggagtgaga acaatctaca
ccattgatgg gctcaagaag atttccagcc tggaccaact ggtggaagga gagagttatg
tatgtggctc catagagccc ttcaagaaac tggagtacac caagaatgtg aaccccaact
ggtcggtgaa cgtcaagacc acctcggctt ctcgggcagt gtcttcactg gccactgcca
aaggaagccc ttcagaggtg cgagagaata aggatttcat tcggcccaag ctggtcacca
tcatcagaag tggcgtgaag ccacggaaag ctgtcaggat tctgctgaac aagaaaacgg
ctcattcctt tgagcaggtc ctcaccgata tcaccgatgc catcaagctg gactcgggag
tggtgaaacg cctgtacacg ttggatggga aacaggtgat gtgccttcag gactttttg
gtgatgatga catttttatt gcatgtggac cggagaagtt ccgttaccgg gatgatttct
tgctagatga aagtgaatgt cgagtggtaa agtccacttc ttacaccaaa atagcttcat
catcccgcag gagcaccacc aagagcccag gaccgtccag gcgtagcaag tcccctgcct
ccaccagctc agttaatgga accctggta gtcagctctc tactccgcgc tcaggcaagt
cgccaagccc atcacccacc agcccaggaa gcctgcggaa gcagagggac ctgtaccgcc
ccctctcttc ggatgacttg gattcagtag gagactcagt gtaaaagaaa SEQ ID NO: 3
Met Ser Phe Gly Arg Asp Met Glu Leu Glu His Phe Asp Glu Arg Asp
1               5                   10                  15
Lys Ala Gln Arg Tyr Ser Arg Gly Ser Arg Val Asn Gly Leu Pro Ser
            20                  25                  30
Pro Thr His Ser Ala His Cys Ser Phe Tyr Arg Thr Arg Thr Leu Gln
        35                  40                  45
Thr Leu Ser Ser Glu Lys Lys Ala Lys Lys Val Arg Phe Tyr Arg Asn
    50                  55                  60
Gly Asp Arg Tyr Phe Lys Gly Ile Val Tyr Ala Ile Ser Pro Asp Arg
65                  70                  75                  80
Phe Arg Ser Phe Glu Ala Leu Leu Ala Asp Leu Thr Arg Thr Leu Ser
                85                  90                  95
Asp Asn Val Asn Leu Pro Gln Gly Val Arg Thr Ile Tyr Thr Ile Asp
            100                 105                 110
Gly Leu Lys Lys Ile Ser Ser Leu Asp Gln Leu Val Glu Gly Glu Ser
        115                 120                 125
Tyr Val Cys Gly Ser Ile Glu Pro Phe Lys Lys Leu Glu Tyr Thr Lys
    130                 135                 140
Asn Val Asn Pro Asn Trp Ser Val Asn Val Lys Thr Thr Ser Ala Ser
145                 150                 155                 160
Arg Ala Val Ser Ser Leu Ala Thr Ala Lys Gly Gly Pro Ser Glu Val
                165                 170                 175
Arg Glu Asn Lys Asp Phe Ile Arg Pro Lys Leu Val Thr Ile Ile Arg
            180                 185                 190
Ser Gly Val Lys Pro Arg Lys Ala Val Arg Ile Leu Leu Asn Lys Lys
        195                 200                 205
Thr Ala His Ser Phe Glu Gln Val Leu Thr Asp Ile Thr Asp Ala Ile
    210                 215                 220
Lys Leu Asp Ser Gly Val Val Lys Arg Leu Tyr Thr Leu Asp Gly Lys
225                 230                 235                 240
Gln Val Met Cys Leu Gln Asp Phe Phe Gly Asp Asp Ile Phe Ile
                245                 250                 255
Ala Cys Gly Pro Glu Lys Phe Arg Tyr Gln Asp Asp Phe Leu Leu Asp
            260                 265                 270

-continued

```
Glu Ser Glu Cys Arg Val Val Lys Ser Thr Ser Tyr Thr Lys Ile Ala
        275             280             285
Ser Ala Ser Arg Arg Gly Thr Thr Lys Ser Pro Gly Pro Ser Arg Arg
        290             295             300
Ser Lys Ser Pro Ala Ser Thr Ser Ser Val Asn Gly Thr Pro Gly Ser
305             310             315             320
Gln Leu Ser Thr Pro Arg Ser Gly Lys Ser Pro Ser Pro Ser Pro Thr
                325             330             335
Ser Pro Gly Ser Leu Arg Lys Gln Arg Asp Leu Tyr Arg Pro Leu Ser
        340             345             350
Ser Asp Asp Leu Asp Ser Gly Asp Ser Val
        355             360

SEQ ID NO: 4
Met Ser Phe Gly Arg Asp Met Glu Leu Glu His Phe Asp Glu Arg Asp
1               5               10              15
Lys Ala Gln Arg Tyr Ser Arg Gly Ser Arg Val Asn Gly Leu Pro Ser
                20              25              30
Pro Thr His Ser Ala His Cys Ser Phe Tyr Arg Thr Arg Thr Leu Gln
            35              40              45
Thr Leu Ser Ser Glu Lys Lys Ala Lys Lys Val Arg Phe Tyr Arg Asn
        50              55              60
Gly Asp Arg Tyr Phe Lys Gly Ile Val Tyr Ala Ile Ser Pro Asp Arg
65              70              75              80
Phe Arg Ser Phe Glu Ala Leu Leu Ala Asp Leu Thr Arg Thr Leu Ser
                85              90              95
Asp Asn Val Asn Leu Pro Gln Gly Val Arg Thr Ile Tyr Thr Ile Asp
            100             105             110
Gly Leu Lys Lys Ile Ser Ser Leu Asp Gln Leu Val Glu Gly Glu Ser
        115             120             125
Tyr Val Cys Gly Ser Ile Glu Pro Phe Lys Lys Leu Glu Tyr Thr Lys
        130             135             140
Asn Val Asn Pro Asn Trp Ser Val Asn Val Lys Thr Thr Ser Ala Ser
145             150             155             160
Arg Ala Val Ser Ser Leu Ala Thr Ala Lys Gly Ser Pro Ser Glu Val
                165             170             175
Arg Glu Asn Lys Asp Phe Ile Arg Pro Lys Leu Val Thr Ile Ile Arg
            180             185             190
Ser Gly Val Lys Pro Arg Lys Ala Val Arg Ile Leu Leu Asn Lys Lys
        195             200             205
Thr Ala His Ser Phe Glu Gln Val Leu Thr Asp Ile Thr Asp Ala Ile
        210             215             220
Lys Leu Asp Ser Gly Val Val Lys Arg Leu Tyr Thr Leu Asp Gly Lys
225             230             235             240
Gln Val Met Cys Leu Gln Asp Phe Phe Gly Asp Asp Asp Ile Phe Ile
                245             250             255
Ala Cys Gly Pro Glu Lys Phe Arg Tyr Gln Asp Asp Phe Leu Leu Asp
            260             265             270
Glu Ser Glu Cys Arg Val Val Lys Ser Thr Ser Tyr Thr Lys Ile Ala
        275             280             285
Ser Ser Ser Arg Arg Ser Thr Thr Lys Ser Pro Gly Pro Ser Arg Arg
        290             295             300
Ser Lys Ser Pro Ala Ser Thr Ser Ser Val Asn Gly Thr Pro Gly Ser
305             310             315             320
Gln Leu Ser Thr Pro Arg Ser Gly Lys Ser Pro Ser Pro Ser Pro Thr
```

-continued

```
                    325                         330                         335
Ser Pro Gly Ser Leu Arg Lys Gln Arg Asp Leu Tyr Arg Pro Leu Ser
                340                         345                         350

Ser Asp Asp Leu Asp Ser Val Gly Asp Ser Val
            355                         360
```

The invention claimed is:

1. A composition suitable for the treatment of neuroblastoma comprising a pharmaceutically and/or physiologically acceptable carrier and at least one antisense RNA or DNA oligonucleotide comprising one or more sequences selected from the group consisting of SEQ ID NO: 15, SEQ ID NO: 16, SEQ ID NO: 19, and SEQ ID NO: 20.

2. The composition according to claim 1, further comprising one or more targeting compounds, wherein said targeting compounds are capable of targeting neuroblastoma cells in vivo or in vitro.

3. The composition according to claim 2, wherein the targeting compound is an immunoliposome or a monoclonal antibody.

4. The composition according to claim 1, wherein said at least one antisense RNA oligonucleotide comprises 2'-O-methyl RNA or 2'-O-allyl RNA.

5. The composition according to claim 1, wherein said at least one antisense RNA or DNA oligonucleotide comprises Peptide Nucleic Acids.

6. The composition according to claim 1, wherein said at least one antisense RNA or DNA oligonucleotide comprises Locked Nucleic Acids.

7. The composition according to claim 1, wherein the amount of said at least one antisense RNA or DNA oligonucleotide is between 0.05 and 5.0 μmol/ml.

8. A composition comprising a pharmaceutically and/or physiologically acceptable carrier and a nucleic acid sequence comprising SEQ ID NO: 2, or a complement thereof.

9. A composition suitable for the treatment of neuroblastoma comprising at least one antisense RNA or DNA oligonucleotide of 17-23 nucleotides comprising one or more sequences selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and sequences derived thereof in which 1, 2 or 3 nucleotides has been added, replaced or deleted.

10. The composition according to claim 9, further comprising a pharmaceutically and/or physiologically acceptable carrier.

11. The composition according to claim 9, wherein at least one antisense RNA or DNA oligonucleotide comprises Peptide Nucleic Acids.

12. The composition according to claim 9, wherein at least one antisense RNA or DNA oligonucleotide comprises Locked Nucleic Acids.

13. The composition according to claim 9, further comprising a targeting compound, which is capable of targeting neuroblastoma cells in vivo or in vitro.

14. The composition according to claim 13, wherein the targeting compound is an immunoliposome or a monoclonal antibody.

15. The composition according to claim 9, wherein said RNA oligonucleotide comprises 2'-O-methyl RNA or 2'-O-allyl RNA.

16. The composition according to claim 9, wherein the amount of said at least one antisense RNA or DNA oligonucleotide is between 0.05 and 5.0 μmol/ml.

* * * * *

SEQUENCE LISTING

<160> NUMBER OF SEQ ID NOS: 28

<210> SEQ ID NO 1
<211> LENGTH: 1283
<212> TYPE: DNA
<213> ORGANISM: Mus musculus

<400> SEQUENCE: 1

```
ccacgcgtcc gcggagaacc gcatttcaat gaggaccagc tccagcgcat cagtgcacta      60
gcggtcgcag cttccagacg ctcgtgctcc gcagccccag ccgcgcccag ccggcgagg      120
acagctccag cagccggcca cagacaaccc agcctccacc cgcgaccggt tccataagca     180
agccagccat gtcgttcggc agagatatgg agttggagca ttttgatgag cgggacaagg     240
cgcagaggta cagcaggggg tcccgtgtga atggcctgcc cagccccaca cacagcgccc     300
actgcagctt ctaccgcacc cgcaccctgc agacactcag ctccgagaag aaagccaaga     360
aggttcgatt ctacagaaat ggtgaccgct acttcaaagg aattgtgtat gccatctccc     420
cagaccgctt cagatctttc gaggccctgc tggctgattt gacccgaact ctctcggata     480
atgtgaattt gccccagggg gtgagaacca tctacaccat cgatggactc aagaagatct     540
ccagcctgga ccagctggtg aaggtgaaa gctatgtctg cggctccatc gagcccttta     600
agaagctgga gtacaccaag aatgtgaacc caactggtc agtgaacgtc aagaccacct     660
cagcctcccg cgcagtgtct tctttggcca ctgccaaggg tgggccttcg gaggttcggg     720
agaataagga tttcattcga cccaagctgg tcaccatcat cagaagtggg gtgaagccac     780
ggaaggctgt cagaatcctg ctgaacaaga gacggctca ctccttcgag caggttctca     840
ctgacattac cgacgctatc aagctggact ccggtgtggt gaagcgcctg tacactctgg     900
atgggaagca ggtgatgtgc cttcaggact ttttggtga cgatgacatt tttattgcat     960
gtggaccaga gaagttccgt taccaggatg atttcttgct agatgaaagt gaatgtgag    1020
tggtgaaatc aacttcttac accaaaatag catcagcgtc ccgcagaggc acaaccaaga    1080
gcccaggacc ttcccggaga agcaagtccc cagcctccac cagctcagtt aatgaaccc    1140
ctggtagtca gctctctact ccacgctcgg gcaagtcacc aagtccatca cccaccagcc    1200
caggaagcct gcggaagcag agggacctgt accgcccct ctcgtcggat gatttggact    1260
caggagactc agtgtaagaa ttc                                           1283
```

<210> SEQ ID NO 2
<211> LENGTH: 1310
<212> TYPE: DNA
<213> ORGANISM: Homo sapiens

<400> SEQUENCE: 2

```
gcacatccct gcactagtgg ccgcaaccga gacgccgcgc tcagcagct gctgccgccc      60
agcccggccc cgccgccgcc cccagcccct gcagccccga gccccggcc gcgcccagcc    120
```

```
cggcgaggac agcaccagga ggcggccccc agcgcggcca caaagacccc cggcggcgtc    180
tctccgcgga ccggtcctac ttgaagtcca tcatgtcctt cggcagagac atggagctgg    240
agcacttcga cgagcgggat aaggcgcaga gatacagccg agggtcgcgg gtgaacggcc    300
tgccgagccc gacgcacagc gcccactgca gcttctaccg cacccgcacg ctgcagacgc    360
tcagctccga gaagaaggcc aagaaagttc gtttctatcg aaacggagat cgatacttca    420 aaggattgt gtatgccatc tccccagacc ggttccgatc ttttgaggcc ctgctggctg     480
atttgacccg aactctgtcg gataacgtga atttgcccca gggagtgaga acaatctaca    540
ccattgatgg gctcaagaag atttccagcc tggaccaact ggtggaagga gagagttatg    600
tatgtggctc catagagccc ttcaagaaac tggagtacac caagaatgtg aaccccaact    660
ggtcggtgaa cgtcaagacc acctcggctt ctcgggcagt gtcttcactg gccactgcca    720
aaggaagccc ttcagaggtg cgagagaata aggatttcat tcggcccaag ctggtcacca    780
tcatcagaag tggcgtgaag ccacggaaag ctgtcaggat tctgctgaac aagaaaacgg    840
ctcattcctt tgagcaggtc ctcaccgata tcaccgatgc catcaagctg gactcgggag    900
tggtgaaacg cctgtacacg ttggatggga acaggtgat gtgccttcag actttttttg     960
gtgatgatga cattttttatt gcatgtggac cggagaagtt ccgttaccag gatgatttct   1020
tgctagatga aagtgaatgt cgagtggtaa agtccacttc ttacaccaaa atagcttcat   1080
catcccgcag gagcaccacc aagagcccag gaccgtccag gcgtagcaag tccctgcct    1140 ccaccagctc agttaatgga acccctggta gtcagctctc tactccgcgc tcaggcaagt   1200
cgccaagccc atcacccacc agcccaggaa gcctgcggaa gcagagggac ctgtaccgcc   1260
ccctctcttc ggatgacttg gattcagtag gagactcagt gtaaaagaaa             1310
```

```
<210> SEQ ID NO 3
<211> LENGTH: 362
<212> TYPE: PRT
<213> ORGANISM: Mus musculus

<400> SEQUENCE: 3

Met Ser Phe Gly Arg Asp Met Glu Leu Glu His Phe Asp Glu Arg Asp
 1               5                  10                  15

Lys Ala Gln Arg Tyr Ser Arg Gly Ser Arg Val Asn Gly Leu Pro Ser
            20                  25                  30

Pro Thr His Ser Ala His Cys Ser Phe Tyr Arg Thr Arg Thr Leu Gln
        35                  40                  45

Thr Leu Ser Ser Glu Lys Lys Ala Lys Lys Val Arg Phe Tyr Arg Asn
    50                  55                  60

Gly Asp Arg Tyr Phe Lys Gly Ile Val Tyr Ala Ile Ser Pro Asp Arg
65                  70                  75                  80

Phe Arg Ser Phe Glu Ala Leu Leu Ala Asp Leu Thr Arg Thr Leu Ser
                85                  90                  95

Asp Asn Val Asn Leu Pro Gln Gly Val Arg Thr Ile Tyr Thr Ile Asp
           100                 105                 110

Gly Leu Lys Lys Ile Ser Ser Leu Asp Gln Leu Val Glu Gly Glu Ser
       115                 120                 125

Tyr Val Cys Gly Ser Ile Glu Pro Phe Lys Lys Leu Glu Tyr Thr Lys
   130                 135                 140

Asn Val Asn Pro Asn Trp Ser Val Asn Val Lys Thr Thr Ser Ala Ser
145                 150                 155                 160

Arg Ala Val Ser Ser Leu Ala Thr Ala Lys Gly Gly Pro Ser Glu Val
```

```
                    165                 170                 175
Arg Glu Asn Lys Asp Phe Ile Arg Pro Lys Leu Val Thr Ile Ile Arg
            180                 185                 190
Ser Gly Val Lys Pro Arg Lys Ala Val Arg Ile Leu Leu Asn Lys Lys
        195                 200                 205
Thr Ala His Ser Phe Glu Gln Val Leu Thr Asp Ile Thr Asp Ala Ile
    210                 215                 220
Lys Leu Asp Ser Gly Val Val Lys Arg Leu Tyr Thr Leu Asp Gly Lys
225                 230                 235                 240
Gln Val Met Cys Leu Gln Asp Phe Phe Gly Asp Asp Ile Phe Ile
                245                 250                 255
Ala Cys Gly Pro Glu Lys Phe Arg Tyr Gln Asp Asp Phe Leu Leu Asp
            260                 265                 270
Glu Ser Glu Cys Arg Val Val Lys Ser Thr Ser Tyr Thr Lys Ile Ala
        275                 280                 285
Ser Ala Ser Arg Arg Gly Thr Thr Lys Ser Pro Gly Pro Ser Arg Arg
    290                 295                 300
Ser Lys Ser Pro Ala Ser Thr Ser Ser Val Asn Gly Thr Pro Gly Ser
305                 310                 315                 320
Gln Leu Ser Thr Pro Arg Ser Gly Lys Ser Pro Ser Pro Ser Pro Thr
                325                 330                 335
Ser Pro Gly Ser Leu Arg Lys Gln Arg Asp Leu Tyr Arg Pro Leu Ser
            340                 345                 350
Ser Asp Asp Leu Asp Ser Gly Asp Ser Val
        355                 360

<210> SEQ ID NO 4
<211> LENGTH: 363
<212> TYPE: PRT
<213> ORGANISM: Homo sapiens

<400> SEQUENCE: 4

Met Ser Phe Gly Arg Asp Met Glu Leu Glu His Phe Asp Glu Arg Asp
1               5                   10                  15
Lys Ala Gln Arg Tyr Ser Arg Gly Ser Arg Val Asn Gly Leu Pro Ser
            20                  25                  30
Pro Thr His Ser Ala His Cys Ser Phe Tyr Arg Thr Arg Thr Leu Gln
        35                  40                  45
Thr Leu Ser Ser Glu Lys Lys Ala Lys Lys Val Arg Phe Tyr Arg Asn
    50                  55                  60
Gly Asp Arg Tyr Phe Lys Gly Ile Val Tyr Ala Ile Ser Pro Asp Arg
65                  70                  75                  80
Phe Arg Ser Phe Glu Ala Leu Leu Ala Asp Leu Thr Arg Thr Leu Ser
                85                  90                  95
Asp Asn Val Asn Leu Pro Gln Gly Val Arg Thr Ile Tyr Thr Ile Asp
            100                 105                 110
Gly Leu Lys Lys Ile Ser Ser Leu Asp Gln Leu Val Glu Gly Glu Ser
        115                 120                 125
Tyr Val Cys Gly Ser Ile Glu Pro Phe Lys Lys Leu Glu Tyr Thr Lys
    130                 135                 140
Asn Val Asn Pro Asn Trp Ser Val Asn Val Lys Thr Thr Ser Ala Ser
145                 150                 155                 160
Arg Ala Val Ser Ser Leu Ala Thr Ala Lys Gly Ser Pro Ser Glu Val
                165                 170                 175
```

-continued

```
Arg Glu Asn Lys Asp Phe Ile Arg Pro Lys Leu Val Thr Ile Ile Arg
            180                 185                 190

Ser Gly Val Lys Pro Arg Lys Ala Val Arg Ile Leu Leu Asn Lys Lys
        195                 200                 205

Thr Ala His Ser Phe Glu Gln Val Leu Thr Asp Ile Thr Asp Ala Ile
    210                 215                 220

Lys Leu Asp Ser Gly Val Val Lys Arg Leu Tyr Thr Leu Asp Gly Lys
225                 230                 235                 240

Gln Val Met Cys Leu Gln Asp Phe Phe Gly Asp Asp Ile Phe Ile
                245                 250                 255

Ala Cys Gly Pro Glu Lys Phe Arg Tyr Gln Asp Asp Phe Leu Leu Asp
                260                 265                 270

Glu Ser Glu Cys Arg Val Val Lys Ser Thr Ser Tyr Thr Lys Ile Ala
            275                 280                 285

Ser Ser Ser Arg Arg Ser Thr Thr Lys Ser Pro Gly Pro Ser Arg Arg
        290                 295                 300

Ser Lys Ser Pro Ala Ser Thr Ser Ser Val Asn Gly Thr Pro Gly Ser
305                 310                 315                 320

Gln Leu Ser Thr Pro Arg Ser Gly Lys Ser Pro Ser Pro Ser Pro Thr
                325                 330                 335

Ser Pro Gly Ser Leu Arg Lys Gln Arg Asp Leu Tyr Arg Pro Leu Ser
            340                 345                 350

Ser Asp Asp Leu Asp Ser Val Gly Asp Ser Val
        355                 360

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
caagaagacg gcucacucct t                                           21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
ggagugagcc gucuucuugt t                                           21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 7
caagaaaacg gcucauucct t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
ggaaugagcc guuucuugt t                                               21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
gaaagccaag aagguucgat t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
tcgaaccuuc uuggcuuuct t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
gaaggccaag aaaguucgut t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
``` oligonucleotide

<400> SEQUENCE: 12
acgaacuuuc uuggccuuct t                                              21

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gcugggcagg ccauucacac                                                20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gcucggcagg ccguucaccc                                                20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cuucucggag cugagugucu                                                20

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
cuucucggag cugagcgucu                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gctgggcagg ccattcacac                                                20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 18
gctcggcagg ccgttcaccc                                                20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cttctcggag ctgagtgtct                                                20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cttctcggag ctgagcgtct                                                20

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctggaattct tacactgagt ctcctgag                                       28

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcaggttctc actgacatta ccg                                            23

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccaggatcca ccatgtcgtt cggcagagat atg                                 33

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 24
tttgctgtta gatgcttgct taggaaatgg gaaaccttga        40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tttgatgtta tatgcttgat taggacatgg gacacctgga        40

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
caagaagacg gcucacucc        19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ggagugagcc gucuucuug        19

<210> SEQ ID NO 28
<211> LENGTH: 365
<212> TYPE: PRT
<213> ORGANISM: Mus musculus

<400> SEQUENCE: 28

Met Glu Leu Asp Phe Gly His Phe Asp Glu Arg Asp Lys Ala Ser Arg
 1               5                  10                  15

Asn Met Arg Gly Ser Arg Met Asn Gly Leu Pro Ser Pro Thr His Ser
                20                  25                  30

Ala His Cys Ser Phe Tyr Arg Thr Arg Thr Leu Gln Ala Leu Ser Asn
            35                  40                  45

Glu Lys Lys Ala Lys Lys Val Arg Phe Tyr Arg Asn Gly Asp Arg Tyr
        50                  55                  60

Phe Lys Gly Ile Val Tyr Ala Val Ser Ser Asp Arg Phe Arg Ser Phe
    65                  70                  75                  80

Asp Ala Leu Leu Ala Asp Leu Thr Arg Ser Leu Ser Asp Asn Ile Asn
                85                  90                  95

Leu Pro Gln Gly Val Arg Tyr Ile Tyr Thr Ile Asp Gly Ser Arg Lys
                100                 105                 110

Ile Gly Ser Met Asp Glu Leu Glu Glu Gly Glu Ser Tyr Val Cys Ser
            115                 120                 125

Ser Asp Asn Phe Phe Lys Lys Val Glu Tyr Thr Lys Asn Val Asn Pro
        130                 135                 140

Asn Trp Ser Val Asn Val Lys Thr Ser Ala Asn Met Lys Ala Pro Gln

-continued

```
            145                 150                 155                 160
        Ser Leu Ala Ser Ser Asn Ser Ala Gln Ala Arg Glu Asn Lys Asp Phe
                        165                 170                 175
        Val Arg Pro Lys Leu Val Thr Ile Ile Arg Ser Gly Val Lys Pro Arg
                        180                 185                 190
        Lys Ala Val Arg Val Leu Leu Asn Lys Lys Thr Ala His Ser Phe Glu
                        195                 200                 205
        Gln Val Leu Thr Asp Ile Thr Glu Ala Ile Lys Leu Glu Thr Gly Val
                        210                 215                 220
        Val Lys Lys Leu Tyr Thr Leu Asp Gly Lys Gln Val Thr Cys Leu His
        225                 230                 235                 240
        Asp Phe Phe Gly Asp Asp Val Phe Ile Ala Cys Gly Pro Glu Lys
                        245                 250                 255
        Phe Arg Tyr Ala Gln Asp Asp Phe Ser Leu Asp Glu Asn Glu Cys Arg
                        260                 265                 270
        Val Met Lys Gly Asn Pro Ser Ala Ala Gly Pro Lys Ala Ser Pro
                        275                 280                 285
        Thr Pro Gln Lys Thr Ser Ala Lys Ser Pro Gly Pro Met Arg Arg Ser
                        290                 295                 300
        Lys Ser Pro Ala Asp Ser Gly Asn Asp Gln Asp Ala Asn Gly Thr Ser
        305                 310                 315                 320
        Ser Ser Gln Leu Ser Thr Pro Lys Ser Lys Gln Ser Pro Ile Ser Thr
                        325                 330                 335
        Pro Thr Ser Pro Gly Ser Leu Arg Arg His Lys Asp Leu Tyr Leu Pro
                        340                 345                 350
        Leu Ser Leu Asp Asp Ser Asp Ser Leu Gly Asp Ser Met
                        355                 360                 365
```